US006338709B1

(12) United States Patent
Geoffrion et al.

(10) Patent No.: US 6,338,709 B1
(45) Date of Patent: *Jan. 15, 2002

(54) INTRAVASCULAR RADIATION THERAPY DEVICE AND METHOD OF USE

(75) Inventors: Richard P. Geoffrion, Livermore; Gholam Reza Zadno-Azizi, Newark; Samuel L. Omaleki, Morgan Hill, all of CA (US)

(73) Assignee: Medtronic PercuSurge, Inc., Sunnyvale, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/026,103

(22) Filed: Feb. 19, 1998

(51) Int. Cl.[7] .................................................. A61N 5/00
(52) U.S. Cl. ............................................................ 600/3
(58) Field of Search ........................................ 600/1–8

(56) References Cited

U.S. PATENT DOCUMENTS

| | | | |
|---|---|---|---|
| 4,423,725 A | 1/1984 | Baran et al. |
| 4,425,908 A | 1/1984 | Simon |
| 4,445,892 A | 5/1984 | Hussein et al. |
| 4,456,011 A | 6/1984 | Warnecke |
| 4,494,531 A | 1/1985 | Gianturco |
| 4,588,395 A | 5/1986 | Lemelson |
| 4,610,662 A | 9/1986 | Weikl et al. |
| 4,619,246 A | 10/1986 | Molgaard-Nielsen et al. |
| 4,655,746 A | 4/1987 | Daniels et al. |

(List continued on next page.)

FOREIGN PATENT DOCUMENTS

| EP | 0 526 102 A1 | 7/1992 |
|---|---|---|
| EP | 0 784 991 A1 | 7/1997 |
| EP | 0 791 340 A1 | 8/1997 |
| EP | 0 820 784 A2 | 1/1998 |
| EP | 0 826 393 A1 | 3/1998 |
| EP | 0 826 395 A1 | 3/1998 |
| WO | WO 87/07510 | 12/1987 |
| WO | WO 96/01591 | 1/1996 |
| WO | WO 96/39998 | 12/1996 |
| WO | WO 97/40889 | 11/1997 |
| WO | WO 98/33443 | 8/1998 |
| WO | WO 98/46297 | 10/1998 |
| WO | WO 99/20324 | 4/1999 |
| WO | WO 99/40962 | 8/1999 |

OTHER PUBLICATIONS

Ron Waksman, MD, Local Catheter–Based Intracoronary Radiation Therapy for Restenosis, *The American Journal of Cardiology*, vol. 78 (3A) Aug. 14, 1996, pp. 23–28.

Ron Waksman, MD, Radiation Therapy For In–stent Restenosis: A New Dimension, *Asia Pacific Heart J*, Proceedings of Coronary Stenting Supplement, 1997, pp. 61–62.

Ron Waksman, MD, Effect of Intravascular Irradiation on Cell Proliferation, Apoptosis, and Vascular Remodeling After Balloon Overstretch Injury of Porcine Coronary Arteries, *Circulation*, vol. 96, No. 6, Sep. 16, 1997, pp. 1944–1952.

(List continued on next page.)

*Primary Examiner*—John P. Lacyk
(74) *Attorney, Agent, or Firm*—Knobbe, Martens, Olson & Bear, LLP

(57) ABSTRACT

A radiation delivering catheter is positioned away from the walls of the vessel to be treated, e.g. at a stenosis site, so that the radiation flux impacting the walls is more uniform. In one embodiment, one or more balloons are used, and in another, one or more expandable structures. In other embodiments, a radiation source residing within a balloon is shielded from the vessel walls when the balloon is not inflated, but exposes the vessel walls to radiation when the balloon is inflated.

57 Claims, 18 Drawing Sheets

U.S. PATENT DOCUMENTS

| | | |
|---|---|---|
| 4,696,668 A | 9/1987 | Wilcox |
| 4,723,549 A | 2/1988 | Wholey et al. |
| 4,733,653 A | 3/1988 | Leung et al. |
| 4,744,366 A | 5/1988 | Jang |
| 4,747,406 A | 5/1988 | Nash |
| 4,763,654 A | 8/1988 | Jang |
| 4,794,928 A | 1/1989 | Kletschka |
| 4,832,055 A | 5/1989 | Palestrant |
| 4,873,978 A | 10/1989 | Ginsburg |
| 4,926,858 A | 5/1990 | Gifford, III et al. |
| 4,958,634 A | 9/1990 | Jang |
| 5,071,406 A | 12/1991 | Jang |
| 5,090,958 A | 2/1992 | Sahota |
| 5,152,277 A | 10/1992 | Honda et al. |
| 5,158,540 A | 10/1992 | Wijay et al. |
| 5,160,321 A | 11/1992 | Sahota |
| 5,163,905 A | 11/1992 | Don Michael |
| 5,167,239 A | 12/1992 | Cohen et al. |
| 5,188,602 A | 2/1993 | Nichols |
| 5,199,939 A | 4/1993 | Dake et al. |
| 5,213,561 A | 5/1993 | Weinstein et al. |
| 5,226,889 A | 7/1993 | Sheiban |
| 5,256,141 A | 10/1993 | Gencheff et al. |
| 5,267,960 A | 12/1993 | Hayman et al. |
| 5,282,781 A | 2/1994 | Liprie |
| 5,304,132 A | 4/1994 | Jang |
| 5,320,605 A | 6/1994 | Sahota |
| 5,328,471 A | 7/1994 | Slepian |
| 5,329,942 A | 7/1994 | Gunther et al. |
| 5,342,306 A | 8/1994 | Don Michael |
| 5,354,257 A | 10/1994 | Roubin et al. |
| 5,383,856 A | 1/1995 | Bersin |
| 5,395,333 A | 3/1995 | Brill |
| 5,397,307 A | 3/1995 | Goodin |
| 5,411,466 A | 5/1995 | Hess |
| 5,423,744 A | 6/1995 | Gencheff et al. |
| 5,423,846 A | 6/1995 | Fischell |
| 5,429,582 A | 7/1995 | Williams |
| 5,449,343 A | 9/1995 | Samson et al. |
| 5,456,667 A | 10/1995 | Ham et al. |
| 5,460,610 A | 10/1995 | Don Michael |
| 5,462,529 A | 10/1995 | Simpson et al. |
| 5,465,717 A | 11/1995 | Imran et al. |
| 5,484,384 A | 1/1996 | Fearnot |
| 5,484,412 A | 1/1996 | Pierpont |
| 5,490,859 A | 2/1996 | Mische et al. |
| 5,498,227 A | 3/1996 | Mawad |
| 5,501,694 A | 3/1996 | Ressemann et al. |
| 5,503,613 A | 4/1996 | Weinberger |
| 5,505,700 A | 4/1996 | Leone et al. |
| 5,505,701 A | 4/1996 | Anaya Fernandez de Lomana |
| 5,507,768 A | 4/1996 | Lau et al. |
| 5,514,092 A | 5/1996 | Forman et al. |
| 5,520,646 A | 5/1996 | D'Andrea |
| 5,536,250 A | 7/1996 | Klein et al. |
| 5,540,707 A | 7/1996 | Ressemann et al. |
| 5,566,221 A | 10/1996 | Smith et al. |
| 5,599,307 A | 2/1997 | Bacher et al. |
| 5,605,530 A | 2/1997 | Fischell et al. |
| 5,607,445 A | 3/1997 | Summers |
| 5,607,466 A | 3/1997 | Imbert et al. |
| 5,616,114 A | 4/1997 | Thornton et al. |
| 5,624,372 A | 4/1997 | Liprie |
| 5,643,171 A | 7/1997 | Bradshaw et al. |
| 5,653,683 A | 8/1997 | D'Andrea |
| 5,662,580 A | 9/1997 | Bradshaw et al. |
| 5,683,345 A | 11/1997 | Waksman et al. |
| 5,683,411 A | 11/1997 | Kavteladze et al. |
| 5,693,067 A | 12/1997 | Purdy |
| 5,707,332 A | 1/1998 | Weinberger |
| 5,713,828 A | 2/1998 | Coniglione |
| 5,720,717 A | 2/1998 | D'Andrea |
| 5,766,203 A | 6/1998 | Imran et al. |
| 5,769,816 A | 6/1998 | Babut et al. |
| 5,797,948 A | 8/1998 | Dunham |
| 5,814,064 A | 9/1998 | Daniel et al. |
| 5,827,324 A | 10/1998 | Cassell et al. |
| 5,836,968 A | 11/1998 | Simon et al. |
| 5,840,008 A | * 11/1998 | Klein et al. .................... 600/3 |
| 5,851,171 A | 12/1998 | Gasson |
| 5,910,101 A | 6/1999 | Andrews et al. |
| 5,910,154 A | 6/1999 | Tsugita et al. |
| 6,045,495 A | 4/2000 | Weinberger |

OTHER PUBLICATIONS

Ron Waksman, MD, Intracoronary Brachytherapy in the Cath Lab, *Herz,* 1998; 23:401–6(Nr. 6), pp. 401–406.

Local Catheter–Based Intracoronary Radiation Therapy for Restenosis, Ron Waksman, MD, 1996, The American Journal of Cardiology, vol. 78 (3A), Aug. 14, 1996.

Intra–arterial Beta Irradiation Prevents Neointimal Hyperplasia in a Hypercholesterolemic Rabit Restenosis Model, Vitali Verin, MD et al., *Circulation,* vol. 92, No. 8, Oct. 15, 1995.

Percutaneous Removal of Small Gallstones—In Vivo Comparison of Baskets, G.D. Rubin, G.R. Wittich, R.M. Walter, D.C. Swanson, *Journal of Interventional Radiology,* pp. 29–31, 1992.

Long–term Angiographic and Clinical Outcome After Percutaneous Transluminal Coronary Angioplasty and Intracoronary Radiation Therapy in Humans, Jose A Condado, M.D. et al., *Circulation,* vol. 96, Aug. 5, 1997.

Local Catheter–Based Intracoronary Radiation Therapy for Restenosis, Ron Waksman, M.D., *the American Journal of Cardiology,* vol. 78, Aug. 14, 1996.

* cited by examiner

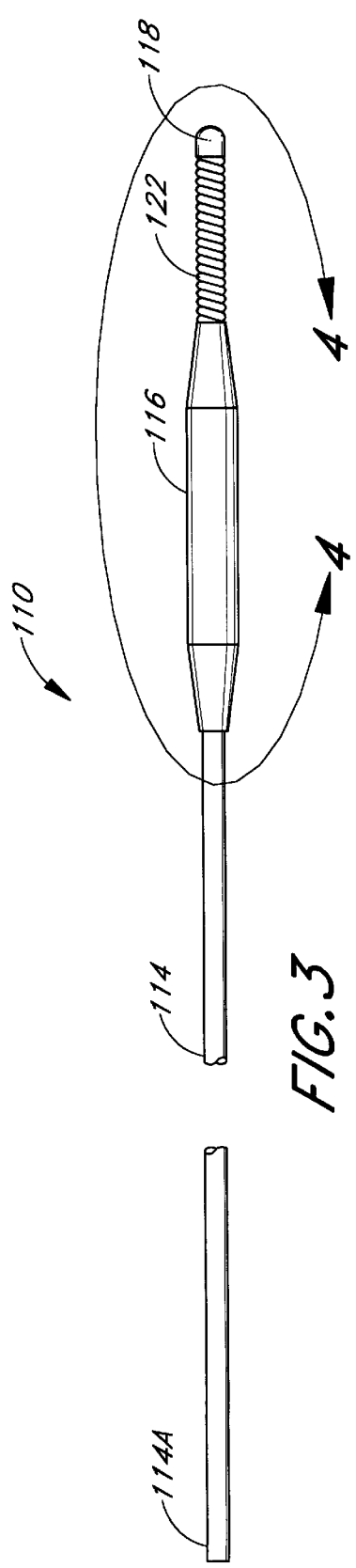
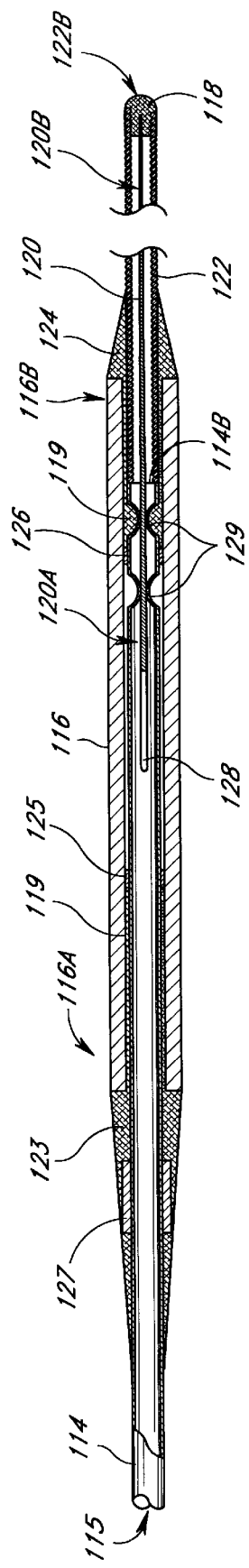
FIG. 3
FIG. 4

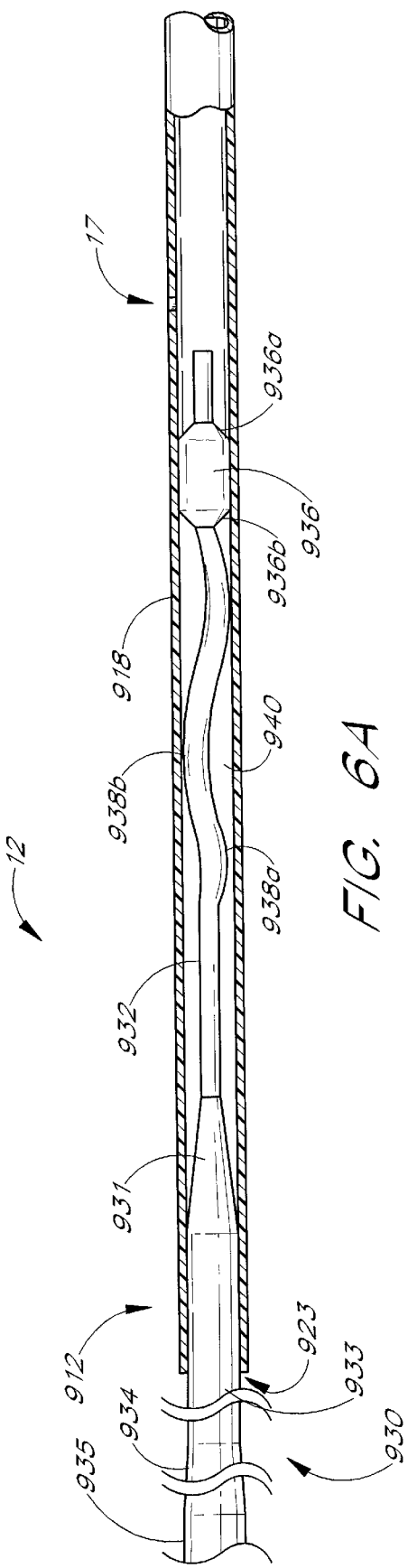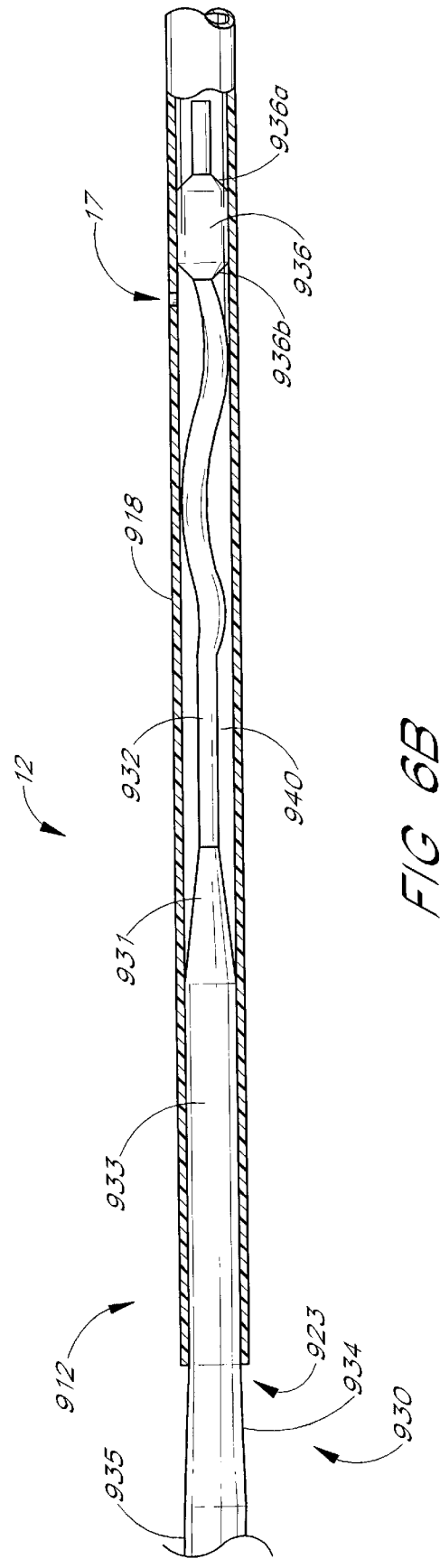

INTRAVASCULAR RADIATION THERAPY DEVICE AND METHOD OF USE

BACKGROUND OF THE INVENTION

1. Field of the Invention

The present invention relates generally to radiation therapy catheters, and, in particular, to an apparatus and method for properly centering or otherwise positioning a radiation therapy catheter within a vascular segment at a desired treatment site.

2. Description of the Related Art

Approximately 20–30% of patients who undergo arterial intervention experience restenosis within about 6 months of the initial treatment. This often necessitates repeating the procedure, such as balloon angioplasty, stent implantation, atherectomy, or treatment with lasers, to once again clear the patient's vascular obstruction. Repeating such a procedure, or undertaking a second, different procedure, is clearly undesirable.

Although stent implantation is used to prevent restenosis, stent restenosis occurs due to neointimal proliferation, i.e. an accelerated growth of tissue at the treated site. However, endovascular radiation effectively inhibits neointimal formation. In particular, a radiation treatment may be undertaken either prior to placement of a conventional stent or through the use of a radioactive stent, i.e. a stent that is coated or impregnated with a radioactive source. The stent may be made radioactive, for example, by placing it in a cyclotron that emits radionuclides.

Radiation therapy undertaken during or after arterial intervention can be accomplished in a variety of ways, as discussed, for example, in U.S. Pat. Nos. 5,213,561 to Weinstein et al., 5,484,384 to Fearnot, and 5,503,613 to Weinberger. Among other radiation therapy devices, these references disclose a guidewire having a radioactive tip, a radioactive source within a balloon catheter, and a radioactive source mounted on a balloon expansible stent. Weinberger teaches that a variety of radiation sources may be used, such as pellets, a wire, or a paste.

One frequently encountered problem is the difficulty in controlling the amount of irradiation; although, a guidewire or catheter type delivery device provides greater control of exposure time than an implanted radioactive stent. Further, a stent should match the length of the vessel segment to be treated; whereas, a guidewire or catheter can be moved axially to increase the length of the vessel exposed to radiation. With a stent, there is also the possibility that the radioactive material will leach into the surrounding tissue, as well as the possibility of thrombosis forming on the stent wire as a delayed re-endotheliatization of the stent struts.

With respect to possible exposure of the clinician or patient to radioactive material, it is easier to control exposure with a guidewire or catheter device. A sleeve or the like suitable for shielding the radioactive element can be used until the element is located at the desired treatment site. A radioactive stent, on the other hand, requires handling prior to insertion into the patient, and can result in increased radiation exposure. Also, it can be even more hazardous to handle, inject, and withdraw radioactive fluid from a balloon catheter.

In previous devices, there is also the difficulty in positioning a device at the vessel segment identified for radiation therapy. U.S. Pat. No. 5,199,939 to Dake et al. attempts to address this problem by providing stiffening members within an otherwise flexible member. An axial arrangement of radioactive pellets at the distal end of the device delivers the radioactive dosage. U.S. Pat. No. 5,503,613 to Weinberger discloses a computer-controlled afterloader that accurately places the radiation delivery wire within the blind lumen, which is sealed at its distal tip. Among the inputs to the afterloader are the location of the vessel segment, the diameter of the treatment site, and the radioactive characteristics of the radioactive element.

Unless a radiation dose delivery wire is carefully centered within a blood vessel, a relatively high radiation zone is obtained at that segment of the vessel contacting or closest to the wire, and a lower radiation zone elsewhere. U.S. Pat. Nos. 4,998,932 to Rosen et al. and 5,566,221 to Smith et al. disclose the use of balloons that aid in the centering of a catheter within a vessel. A balloon must be adequately inflated so that it contacts the vessel walls without damaging tissue or rupturing. If inflating the balloon causes enlargement of the vessel at the treatment site, the increased radius diminishes the level of radiation reaching the vessel walls. For example, irradiating tissue to a depth of about 2–3 mm within the tissue is usually desirable. A change in the diameter of the vessel diminishes the accuracy of the coordinates used by an afterloader, and the radioactive material may lack the intensity required for the desired penetration. If the balloon ruptures, pieces of the balloon may be carried downstream.

Other uses of balloons in radiation delivery include a segmented balloon centering device (see Verin et al., "Intraarterial beta irradiation prevents neointimal hyperplasia in a hypercholesterolemic rabbit restenosis model," *Circulation*, vol. 92, pp. 2284–2290, 1995) and a helical balloon, which is said to provide better flow around the catheter (see R. Waksman, "Local Catheter-Based Intracoronary Radiation Therapy for Restenosis", *The American Journal of Cardiology*, vol. 78, p. 24, 1996).

Thus, there is still a need for a radiation delivering catheter that can be accurately and easily centered within a vascular segment.

SUMMARY OF THE INVENTION

The present invention satisfies the need for a device that can be accurately centered within a vessel to be radioactively treated. By accurately centering a radiation catheter within the vessel, the walls of the vessel to be treated, e.g. at a site of a stenosis, are exposed to radiation flux that is more uniform than it would be if the radiation catheter were in contact with (e.g., resting on) the vessel wall.

In the present invention, various means are utilized to properly position a radiation treatment device within the vessel. In one embodiment of the present invention, one or more balloons are employed to position a radiation delivering catheter within the vessel and away from the vessel wall. In another embodiment of the invention, expandable structures are used to do the same. In yet another embodiment of the invention, a radiation source residing within a balloon is shielded from the vessel walls when the balloon is not inflated, but exposes the vessel walls to radiation when the balloon is inflated.

In one embodiment, a self-centering radiation device for treating a segment of a vessel in a patient comprises a catheter for delivering radiation, a plurality of balloons for securing the radiation catheter within the vessel (in which at least two of the balloons are independently inflatable), and a radioactive source for treating the vascular segment, in which the radioactive source is in proximity with the radiation catheter and positioned near the balloons during treatment.

In another embodiment of the invention, a radiation device for treating a segment of a vessel in a patient comprises a catheter for delivering radiation, a radioactive source in proximity with the radiation catheter, a noncompliant balloon around the radioactive source, a lumen within the radiation catheter that is in fluid communication with the noncompliant balloon to permit inflation and deflation of the noncompliant balloon, and a compliant balloon that surrounds the noncompliant balloon. The compliant balloon expands as the noncompliant balloon expands to radioactively treat the vascular segment.

In another embodiment of the invention, a radiation device for treating a segment of a vessel in a patient comprises a catheter for delivering radiation, a radioactive source in proximity with the radiation catheter, a balloon around the radioactive source, and a lumen within the radiation catheter that is in fluid communication with the balloon, permitting inflation and deflation of the balloon. The balloon has strips of material thereon that substantially shield the surroundings from unwanted radioactive exposure when the balloon is not inflated, in which the area between the strips increases as the balloon expands to more directly expose the vascular segment to radioactive treatment.

Another embodiment of the invention is a self-centering radiation device for treating a segment of a vessel that comprises a catheter for delivering radiation, at least one expandable structure for securing the radiation catheter within the vessel, and a radioactive source for treating the vascular segment, in which the radioactive source is in proximity with the radiation catheter. The expandable structures may be self-expanding and the device may further comprise one or more sheaths for expanding and compressing the expandable structures.

The invention further includes methods of treating a segment of a vessel. One method comprises inserting a catheter into the vessel, inserting a plurality of balloons into the vessel (in which at least two of the balloons are independently inflatable), inflating at least two of the independently inflatable balloons to position the catheter away from the walls of the vessel, and exposing the vascular segment to radiation treatment.

Another method of treating a segment in a vessel comprises inserting a balloon into the vessel, placing the balloon near the vascular segment to be treated, and expanding the balloon to expose the vascular segment to radiation that is located in the balloon's interior.

Yet another method of treating a segment in a vessel comprises inserting a catheter into the vessel, inserting at least one expandable structure into the vessel, expanding the structure to position the catheter away from the walls of the vessel, and treating the vascular segment by exposing it to radiation.

In the embodiments of this invention, radiation can be delivered to the stenosis site by, for example, bonding a radioactive source directly onto the radiation catheter, or by passing radioactive carriers through a lumen within the radiation catheter. For example, the radioactive carriers, which may be in the shape of cylinders or spheres, can be carried towards (or away from) the stenosis site by fluid that is forced into (or out of) the lumen.

BRIEF DESCRIPTION OF THE DRAWINGS

FIG. 3 is a schematic view of an occlusion catheter apparatus for use in the method of the present invention.

FIG. 4 is a schematic cross-sectional view of a distal portion of the catheter apparatus shown in FIG. 3.

FIGS. 6A and 6B show open and closed positions, respectively, of the sealing member, which is used with the balloon catheter of FIGS. 5 and 7.

DETAILED DESCRIPTION OF THE PREFERRED EMBODIMENTS

Figure 1:
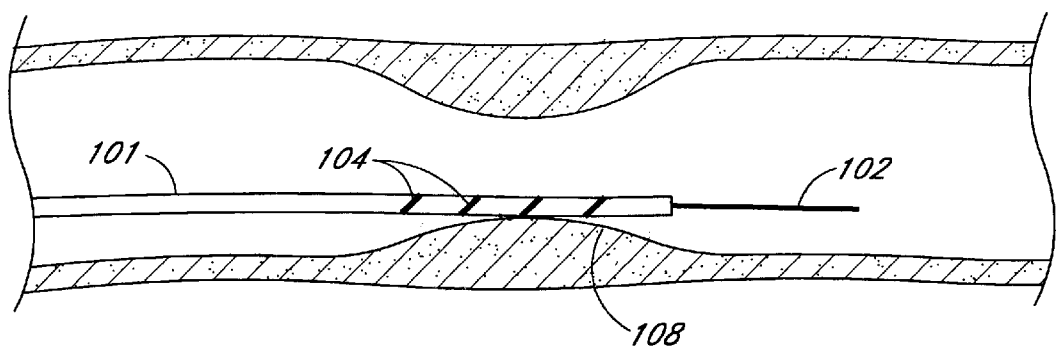
FIG. 1 is a longitudinal cross sectional view of a radiation delivering catheter in the prior art.

FIG. 1 schematically shows a conventional radiation therapy catheter 101 being used with a guidewire 102 for placement within a vessel segment, in which the catheter 101 rests against one side 108 of the wall of the blood vessel. Within the catheter 101 is a radioactive source 104 that is also concentrated against one side 108 of the vessel wall. That is, a zone of higher radiation exists along the line of contact, and a lower radiation zone exists along that portion of the vessel wall not in direct contact with the catheter 101.

In the preferred embodiments of the devices and methods described herein, "centering" and the like are not be narrowly construed, but include the positioning of a catheter at or near the center of a vessel segment, or otherwise positioning the catheter symmetrically or asymmetrically within the vessel segment at a desired treatment location.

Radiation Centering Embodiments Using One or More Balloons

1. Single Distal Balloon

Figure 2A:
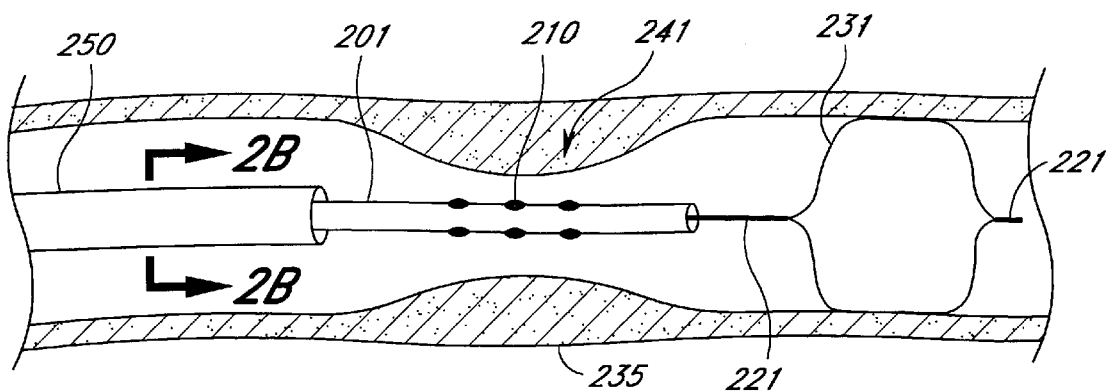
FIG. 2A is a longitudinal cross sectional view of one embodiment of the present invention in which a single balloon is used which is located at the distal end.
Figure 2B:
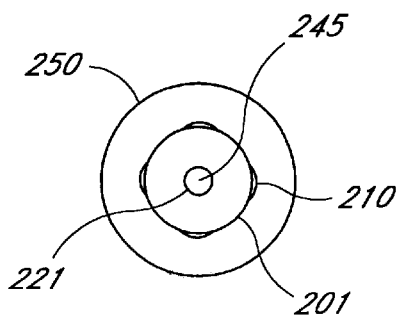
FIG. 2B is an end cross sectional view of the embodiment of FIG. 2A.

FIGS. 2A and 2B, on the other hand, illustrate an embodiment of the present invention in which a catheter 201 (preferably having an I.D. (inside diameter) of 0.018 to 0.042" and an O.D. (outside diameter) of 0.035 to 0.070", with a 100 cm long 73D Pebax™ relatively hard proximal end, and a 20 cm long 35D Pebax™ relatively soft distal end) has a radiation source 210 bonded directly to its outer surface. Alternatively, radiation may be delivered through lumens in the form of radioactive fluid (e.g. a radiochemical), pellets, or wires, as discussed more fully below in connection with FIGS. 8A, 8B, 9A, 9B, and 9C, techniques which limit exposure to medical personnel. In addition, X-ray radiation may be generated within the patient at the treatment site using a small metallic object that is tied to an electrical source.

A catheter 221, which functions as a guidewire, is located within the radiation catheter 201 has a balloon 231 (the balloons herein may be elastomeric, nonelastomeric, or composite) at its distal end. The guidewire 221 permits the clinician to direct the radiation catheter 201 through the vessel 235. As seen more clearly in FIG. 2B, the interior 245 of the guidewire 221 is preferably hollow to permit the balloon 231 to be alternately inflated and deflated with contrast fluid or a saline solution. A number of guidewire technologies for guiding a device through the patient's vessel 235 may be used in this and the other embodiments, such as an integral guidewire tip, a single operator guidewire, or the exchange catheter method, as is well known in the art.

When the balloon 231 is inflated, it tends to center the radiation catheter 201 so that radiation is delivered to the site of the stenosis 241 with better radial symmetry. The best results are obtained when the balloon 231 is located within about 4 cm of the stenosis site 241 (the balloon being on the distal side of the stenosis site), so that during treatment the radiation source 210 remains substantially centrally located within the vessel at the stenosis site 241. Thus, the level of radiation is nearly uniform along the radiation catheter 201 at the stenosis site 241, i.e. the vessel segment to be treated. A movable shield catheter 250 (preferably made of Nylon, Pebax™, or polyethylene, and of size 6–8 F with an I.D. of 0.060–0.090" and an O.D. of 0.080–0.140") may be used when the stenosis site 241 is not being treated, to shield surrounding tissue and clinical personnel from being exposed to radiation. The movable shield catheter 250 preferably comprises a nontoxic heavy metal (such as gold, nitinol, or stainless steel) or a polymer.

The stenosis site 241 is preferably accessed through a port in the patient using an introducer (not shown). Generally, the guidewire 221 is inserted to locate the site of stenosis 241 (or restenosis, as the case may be), and then the radiation and shield catheters 201 and 250 are slid over the guidewire to the treatment site 241. A fluoroscopic procedure may first be used to identify the stenosis site 241, as is known to those skilled in the art.

Preferably, the guidewire 221 has a circular cross section with an outside diameter (O.D.) between about 0.010" and 0.014", but the O.D. may be as great as 0.044", whereas the inner diameter (I.D.) is preferably between about 0.008" to 0.020", and more preferably about 0.009" for a wire having an O.D. of 0.014". The guidewire 221 is preferably made from stainless steel, or, alternatively, an alloy of nickel and titanium known as nitinol. The guidewire 221 is preferably of length 190 to 300 cm and includes a tip and a 35 mm platinum coil which are not shown explicitly in FIG. 2A. Other biocompatible elongate flexible tubes made of polymeric materials such as nylon, polyamide, polyimide, polyethylenes, or combinations thereof, are appropriate for use with the present invention and are described in assignee's co-pending U.S. application Ser. No. 08/812,876, filed Mar. 6, 1997, which is entitled HOLLOW MEDICAL WIRES AND METHODS OF CONSTRUCTING SAME, now U.S. Pat. No. 6,068,623, the entirety of which is hereby incorporated by reference.

The balloon 231 is preferably made of a block copolymer of styrene-ethylene-butylene-styrene (SEBS) such as C-Flex (TM) available from Consolidated Polymer Technologies. More preferably, the balloon material is C-Flex (TM) resin grade R70-050-000, as described in assignee's co-pending U.S. application Ser. No. 09/026,225, filed Feb. 19, 1998 and entitled BALLOON CATHETER AND METHOD OF MANUFACTURE, which is hereby incorporated by reference. Alternatively, the balloon 231 may comprise a conventional compliant expansion balloon made of elastomeric material, such as latex or silicone. The balloon 231 can be attached to the guidewire 221 using the methods described in the application just referenced, or by a conventional method, such as heat bonding or adhesives. For example, a primer such as 7701 LOCTITE (TM) by Loctite Corporation may be used with cyanoacrylate adhesive such as LOCTITE 4011 for attaching a SEBS balloon to a nitinol tube.

The guidewire 221 preferably includes a catheter valve such as that described in assignee's copending U.S. application Ser. No. 08/975,723, filed Nov. 20, 1997 and entitled LOW PROFILE CATHETER VALVE AND INFLATION ADAPTOR, now U.S. Pat. No. 6,050,972, which is a continuation-in-part of application Ser. No. 08/812,139 filed Mar. 6, 1997, now abandoned, which is a continuation-in-part of application Ser. No. 08/650,464, filed May 20, 1996, the entirety of the latest CIP being incorporated by reference. As described in more detail below in connection with FIGS. 6A and 6B, this latest CIP application describes a valve comprising a moveable sealer portion positioned within an inflation lumen, in which the moveable sealer portion may be moved to a position distal of the inflation port, thereby preventing any fluid from being introduced into or withdrawn from the balloon via the inflation port. With this arrangement, the radiation catheter 201 can easily slide off of and onto the guidewire 221 to be positioned within the vessel 235. Preferably, the radiation catheter 201 is inserted into the patient after the guidewire 221 has been positioned within the patient and the balloon 231 has been inflated. A computer-controlled afterloader (not shown) may be used to insert the radiation catheter 201 and control the duration of the radiation therapy. Parameters, such as the location of the treatment site 241 and the diameter of the vessel at that site, are obtained prior to the radiation therapy and are programmed into the afterloader, as is known to those skilled in the art. One source for an afterloader is Nucletron Corporation in Columbia, Md.

The shelf or half-life of the radiation source 210 is important to the dosimetry of the radiation therapy. A "fresh" isotope is preferred to more accurately estimate and control the delivery of a prescribed amount of radiation to a desired tissue depth, such as 14 Gy (or more generally, 8–25 Gy, to a depth of about 2 mm).

In addition, the choice of radioactive isotope is dependent upon the diameter of the vessel 235 and the desired treatment time. For example, a more highly radioactive source may be preferable in a larger diameter vessel, since the treatment time is preferably limited to about 5 minutes or less. Gamma($\gamma$)-emitting sources are generally of higher radioactivity and have a greater half-life than beta($\beta$)-emitting sources. For example, iridium 192 ($^{192}$Ir) has a half life of about 74 days and phosphorus 32 ($^{32}$P) has a half life of about 14.3 days. Other $\beta$-emitting sources, such as Strontium 90/Yttrium ($^{90}$Sr/Y), $^{32}$P or $^{90}$Y may be used. Or, a $\gamma$-emitter such as $^{192}$Ir, iodine 125 ($^{125}$I), or palladium 103 ($^{103}$Pd) may be used. It is also possible to utilize a higher intensity source such as Cobalt 60, although the particular isotope used is not determinate of the benefits of the present invention.

2. A Preferred Catheter with Integral Inflatable Balloon

A catheter suitable for use in the present invention (such as catheter 221) is illustrated in FIGS. 3 and 4. The catheter apparatus 110 is comprised of four communicating members including an elongated tubular member 114, an inflatable balloon member 116 or other expandable medium, a core-wire member 120 and a coil member 122. The catheter apparatus 110 is preferably provided with an outer coating of a lubricous material, such as Teflon.

The tubular member 114 of the catheter apparatus 110 is in the form of hypotubing and is provided with proximal and distal ends 114A and 114B as well as an inner lumen 115 extending along the tubular member 114. The balloon member 116 is coaxially mounted near the distal end 114B of the tubular member 114 by suitable adhesives 119 at a proximal end 116A and a distal end 116B of the balloon member 116 as shown in FIG. 4. Proximal and distal tapered portions 123 and 124 on either side of the balloon 116 preferably include adhesives. Proximal and distal adhesive stops 125 and 126 contact the adhesives 119 to define the working length of the balloon 116. A radiopaque marker 127 is preferably located within the proximal tapered portion 123. A notch 128 in the tubular member 114 permits fluid communication between the lumen 115 and the balloon 116.

A core-wire member 120 of the catheter 110 may be comprised of a flexible wire. The flexible wire 120 is preferably secured to the tubular member 114 within the lumen 115 by a combination of adhesives and crimps 129 (FIG. 4). The proximal end 120A of the flexible wire 120 can have a transverse cross sectional area substantially less than the smallest transverse cross-sectional area of the inner lumen 115 of the tubular member 114. The flexible wire 120 can also taper towards the distal end 120B to smaller diameters to provide greater flexibility to the flexible wire 120. However, the flexible wire 120 may be in the form of a solid rod, ribbon or a helical coil or wire or combinations thereof. As shown in FIG. 4, the distal end 120B of the flexible wire 120 is secured to a rounded plug 118 of solder or braze at the distal end 122B of the coil member 122. The coil member 122 of the catheter 110 may be comprised of a helical coil. The coil member 122 is coaxially disposed about the flexible wire 120, and is secured to the flexible wire 120 by soldering or brazing. Core wires for use in a medical catheter are described in Assignee's co-pending U.S. application Ser. No. 09/026,357, filed Feb. 19, 1998, entitled CORE WIRE WITH SHAPEABLE TIP, now U.S. Pat. No. 6,190,332, which is hereby incorporated by reference.

The balloon member 116 is preferably a compliant balloon formed of a suitable elastic material such as a latex or the like. The flexible coil 122 is preferably formed of a wire of platinum or gold based alloys. The flexible core-wire 120 and the tubular member 114 are preferably formed of a superelastic nickel-titanium alloy.

The catheters of the present invention are preferably provided with a coating on the outer surface, or on both the inner and outer surfaces. Suitable coatings include hydrophilic, hydrophobic and antithrombogenic coatings. Examples include heparin and TEFLON. These coatings can be applied using methods well known in the art. The construction of catheter shafts and notches for fluid communication are discussed in Assignee's co-pending U.S. application Ser. No. 09/026,105, filed Feb. 19, 1998, entitled SHAFT FOR MEDICAL CATHETERS, now U.S. Pat. No. 6,228,072, which is hereby incorporated by reference.

3. A Preferred Inflation Apparatus

Figure 5:
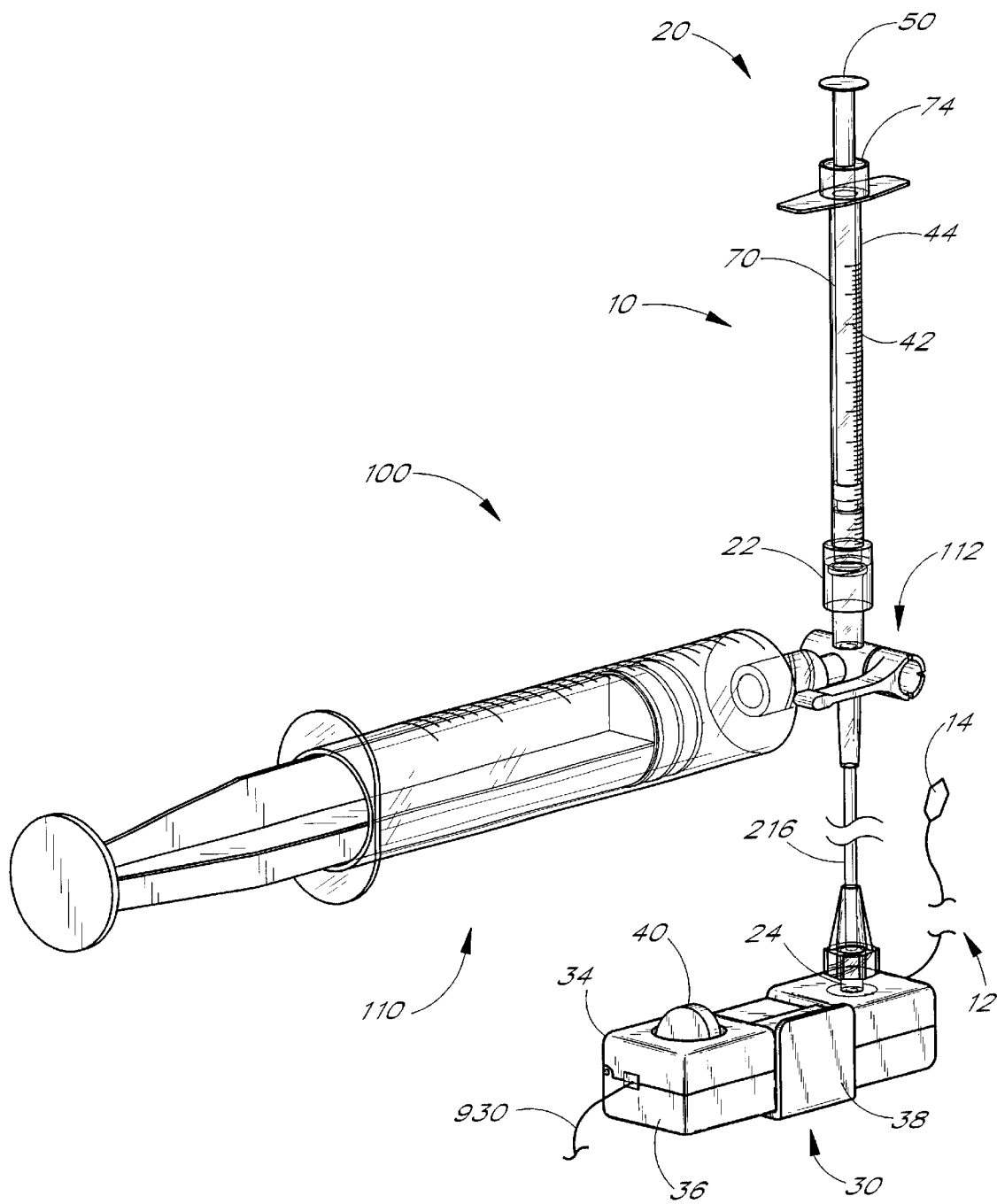
FIG. 5 shows a preferred embodiment of a syringe assembly having features in accordance with the present invention and operably coupled to an illustrative inflation adapter at a proximal portion of a balloon catheter.

A preferred embodiment of a low volume or inflation syringe 10 in a syringe assembly 100 having features in accordance with the present invention is shown in FIG. 5. Also shown in FIG. 5 is an illustrative connection of the assembly 100 to an occlusion balloon guidewire catheter 12 (such as catheter 221) utilizing an inflation adapter 30. The syringe assembly 100, comprising the inflation syringe 10 and a larger capacity or reservoir syringe 110, is attached via tubing 216 to the inflation adapter 30 within which a sealing member 930 (see FIGS. 6A and 6B) and the balloon catheter 12 are engaged during use.

Figure 7:
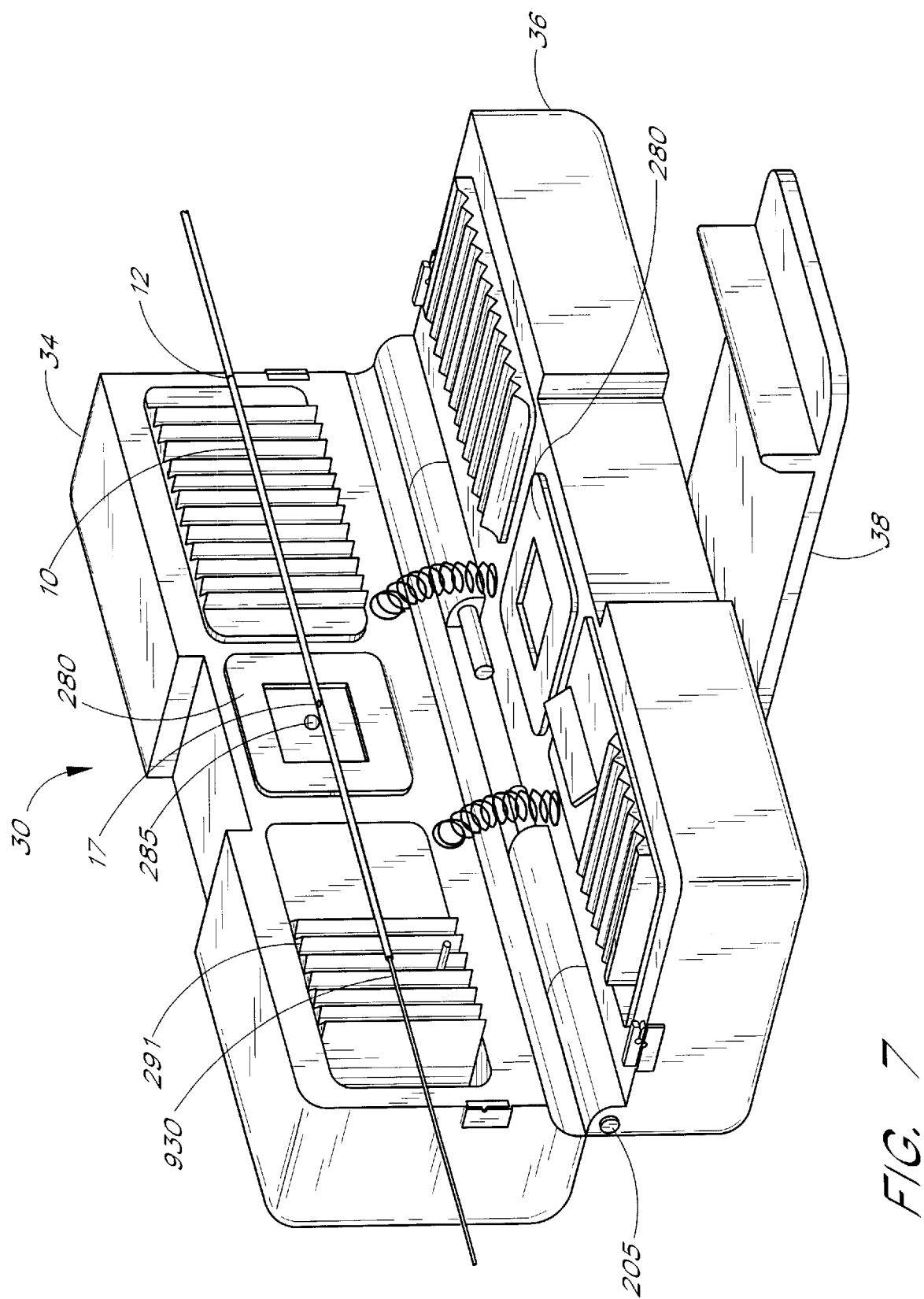
FIG. 7 shows a perspective view of the balloon catheter of FIG. 5 placed within an open inflation adapter.

The sealing member 930, described in more detail below in connection with FIGS. 6A and 6B, is inserted into an open proximal end of the catheter 12. The syringe 10 is used to inject inflation fluid through the adapter 30 and inflation port 17 into a lumen of the catheter 12, and into the balloon 14. The inflation adapter 30, described in more detail below in connection with FIG. 7, is used to open and close the sealing member 930 to permit the inflation or deflation of the balloon 14 mounted on the distal end of the catheter 12. However, it will be emphasized that other types of adapters, valves, and/or sealing members can be employed with the inflation syringe and/or syringe assembly of the present inflation, in order to achieve rapid and accurate inflation/deflation of medical balloons or other nonballoon medical devices. Therefore, although the present inflation is illustrated in connection with a low volume occlusion balloon 14, other types of balloons and nonballoon devices can benefit from the advantages of the invention.

If the balloon 14 is mounted on the distal end of the catheter 12, the syringe 10 and/or syringe assembly 100 is preferably connected at the proximal end of the catheter 12. Prior to use of the syringe 10 to inflate the balloon 14 to the proper size for the vascular segment to be treated, the distal end of the catheter 12 and the balloon 14 are first "primed" or evacuated. The reservoir syringe 110 of the assembly 100 may be used for the evacuation. Access to the vascular site is through a port in the patient obtained, for example, using an introducer (not shown). A preferred system and method for accomplishing the occlusion balloon inflation is described below.

Generally, the inflation syringe 10 of the present invention is provided with a stop mechanism 20 for limiting both the intake of fluid into the syringe and the delivery of fluid from the syringe. The syringe 10 has an elongate cylinder 44 and plunger arrangement 50 which provide for greater displacement or travel by the plunger along the cylinder length than is necessary to expel a relatively small amount of inflation fluid. Thus, with the stop mechanism 20, the clinician is provided with an enhanced sense of whether the fluid in the syringe 10 has been delivered to the balloon, which helps compensate for lack of precision by the clinician. The stop mechanism 20 may be mounted on the syringe 10 during production, or as separate components that can be retro-fit onto an existing supply of syringes.

Referring to FIGS. 5, 6A, 6B, and 7, the catheter 12 has the sealing member 930 inserted into its proximal end and has a side-access inflation port 17, shown in greater detail in FIGS. 6A and 6B. The inflation port 17, proximal end of the catheter 12 and distal end of the sealing member 930 are positioned within the inflation adapter 30 (see FIG. 7) to which a syringe assembly 100 in accordance with the present invention has been operably coupled. The inflation syringe 10 is coupled via an injection cap 22 at its distal end to a valve 112 that also connects the large capacity syringe 110 and a short tube segment 216. The tube segment 216 is adapted to connect to a fitting or male luer member 24 of the inflation adapter 30. Thus, the sealing member 930 is engaged by the adapter 30 to allow use of the low volume syringe 10 of the syringe assembly 100 to inflate the balloon 14 at the end of the catheter 12. Preferably, the sealing member 930 is as described in assignee's previously referenced co-pending U.S. application entitled LOW PROFILE CATHETER VALVE AND INFLATION ADAPTOR.

The catheter 12 (depicted in FIGS. 6A and 6B) has a proximal end 912, and a distal end (not shown in FIGS. 6A and 6B) to which is mounted the inflatable balloon 14. A central lumen 940 extends within a tubular body 918 between the proximal and distal ends. An opening 923 to lumen 940 is present at the proximal end 912 of catheter 12. The inflation port 17 in fluid communication with lumen 940 is provided on tubular body 918.

The sealing member 930 is inserted into lumen 940 through central lumen opening 923. Sealing member 930 has a first region 935 which has an outer diameter substantially the same as the outer diameter of the proximal end 912 of the catheter tubular body. Region 935 has a taper 934, reducing in diameter to a second region 933 which has an outer diameter less than the inner diameter of lumen 940. Region 933 tapers over length 931 to form a plug mandrel wire 932. As a consequence, region 933 and plug mandrel wire 932 are slidably insertable into the proximal opening 923 of catheter 12 and may freely move within lumen 940. In one preferred embodiment, region 935 has an outer diameter of about 0.013 inches, region 933 has an outer diameter of about 0.0086 inches, and plug mandrel wire 932 has a diameter of about 0.005 inches, with region 933 and plug mandrel wire 932 being inserted into a catheter having a central lumen 940 with an inner diameter of about 0.009 inches.

The length of sealing member region 935 extending proximally of catheter 12 may vary in length depending upon the intended use environment. For example, where catheter 12 is to be used as a guide for other catheters in an "over-the-wire" embodiment, it is preferred that the total length of catheter 12 and sealing member region 935 be about 300 centimeters. Alternately, where catheter 12 is to be used in a single operator or rapid exchange embodiment, it is preferred that the total length of catheter 12 and region 935 be about 180 centimeters. Accordingly, with a known catheter length and use environment, an appropriate length for region 935 may be chosen.

Regions 935 and 933 and plug mandrel wire 932 may all be made out of metals such as stainless steel. Alternatively, combinations of materials may be used as well. For example, in some applications it may be desirable to manufacture regions 935 and 933 out of stainless steel, while manufacturing plug mandrel wire 932 out of nitinol. Furthermore, the various sealing member regions may be made from a single metal wire strand coined at various points to achieve the desired dimensional tolerances, or multiple segments may be joined together to form sealing member 930.

Where multiple segments are joined, region 935, region 933, and plug mandrel wire 932 are attached to one another by any suitable means of bonding metal to metal, such as soldering, brazing, adhesives and the like. In one preferred embodiment, cyanoacrylate adhesives are used to adhere these various parts of sealing member 930 to one another.

As illustrated in FIGS. 6A and 6B, the outer diameter of sealing member region 933 is less than the inner diameter of lumen 940, such that region 933 is slidably insertable into lumen 940. In addition, the outer diameters of the tapered portions 931 and wire 932 are also small enough such that they too are slidably insertable in lumen 940. However, the outer diameter of region 935 is greater than the inner diameter 940, and thus only a small portion of tapered portion 934 of sealing member 930 between region 935 and region 933 is insertable into lumen 940 through opening 923. Advantageously, this provides for a snug interference fit when sealing member 930 is fully inserted into catheter 12. This interference fit provides a frictional force which counteracts the tendency of the pressurized fluids and internal wire flexing in the catheter to push sealing member 930 out of opening 923.

As illustrated in FIGS. 6A and 6B, sealing member 930 has movement-force increasing structure which increases the force required to move sealing member 930 within lumen 940. The movement-force increasing structure consists of waves 938a and 938b formed in wire 932 near its distal end. Waves 938a and 938b contact the inner surface of lumen 940, thereby increasing the frictional force which must be overcome to move wire 932 within lumen 940. In one preferred embodiment, wire 932 is made of nitinol and has an outer diameter of about 0.005 inches, and is inserted into a nitinol catheter which has an inner lumen 940 with a diameter of about 0.090 inches, waves are formed on wire 932 for 1-½ cycles with an amplitude of about 0.016 inches to increase the valve-opening movement force.

A lumen sealer portion 936 is coaxially and fixedly mounted on wire 932. Sealer portion 936 forms a fluid tight seal with the outer diameter of wire 932 and the inner diameter of lumen 940, such that fluid introduced into lumen 940 through the inflation port 17 is prevented from flowing past sealer portion 936 when sealer portion 936 is inserted into lumen 940 distally of the inflation port 17. Sealer portion 936 forms the fluid tight seal by firmly contacting the entire inner circumference of a section of lumen 940 along a substantial portion of the length of sealer portion 936.

As shown in FIG. 6A, sealer portion 936 is positioned proximally of the inflation port 17, so that an unrestricted fluid passageway exists between inflation port 17 and the inflatable balloon at the distal end of catheter 12, which is like a valve "open" position. In this position, region 933 is shown partially withdrawn from opening 923. Referring to FIG. 6B, sealer portion 936 is positioned distally of inflation port 17, so that fluid flow between inflation port 17 and the inflatable balloon 14 at the distal end of catheter 12 are substantially blocked, which is like a valve "closed" position.

Catheter 12 is changed from the valve open position to the valve closed position by the movement of sealing member 930 and its various components. Preferably, the exact length of movement needed to change catheter 12 from the valve closed to the valve open position is built into the movement function of the adaptor used to manipulate sealing member 930 thereby opening and closing the catheter valve. In this regard, it is preferred that catheter 12 be used with an adaptor such as adaptor 30, which provides for such controlled precise movement.

The "stroke-length", or overall movement in one dimension, of sealing member 930 required to open or close the valve may be varied depending upon the catheter requirements. When relying upon the inflation adaptor to control movement, however, it is important that the movement of the controlling elements of the adaptor be coordinated with those of sealing member 930. In one embodiment, where the inflation port 17 is positioned 36 mm from opening 923, a stroke length of 5.5 mm was found to be suitable.

Referring to FIGS. 5 and 7, the inflation adapter 30 comprises a housing having two halves 34, 36 preferably formed of metal, medical grade polycarbonate, or the like. The halves 34, 36 are attached by hinges 205 to be separated or joined in a clam shell manner. A locking clip 38 secures the halves while the adapter 30 is in use. A groove within the housing has a width to accept the proximal end of the catheter 12 having the sealing member 930. The male luer member 24 (FIG. 5), or other suitable connector, extrudes from a top of the housing to provide an inflation passageway. Seals 280 are provided within the housing and around the internal segment 285 of the inflation pathway to conduct the pressurized fluid provided by the syringe 10 attached to the male luer member 24.

An actuator 40, shown in FIG. 5 at the top of the adapter housing, controls a cam which operates sliding panels 291 (FIG. 7) contained in the housing. Preferably, the catheter 12 is positioned within the housing with the sealing member 930 in the closed position (FIG. 6B), such that the side inflation port 17 is located in the sealed inflation area 285 of the housing. An adjacent proximal portion of the catheter 12 extends outside the housing (and into the patient), and a proximal portion of the sealing member 930 extends out of the other side of the housing. The locking clip 38 is then secured and then the syringe 10 may be attached. The actuator 40 is moved from a first position to a second position, such that the sliding panels 291 within the housing cause the sealing member 930 to be in an open position to allow fluid flow through the inflation port 17 (FIG. 6A). "Closing" the sealing member 930 is accomplished by moving the actuator 40 from the second position back to the first position (FIG. 6B), such that the balloon inflation is maintained.

4. Multiple Balloon Embodiments

Figure 8A:
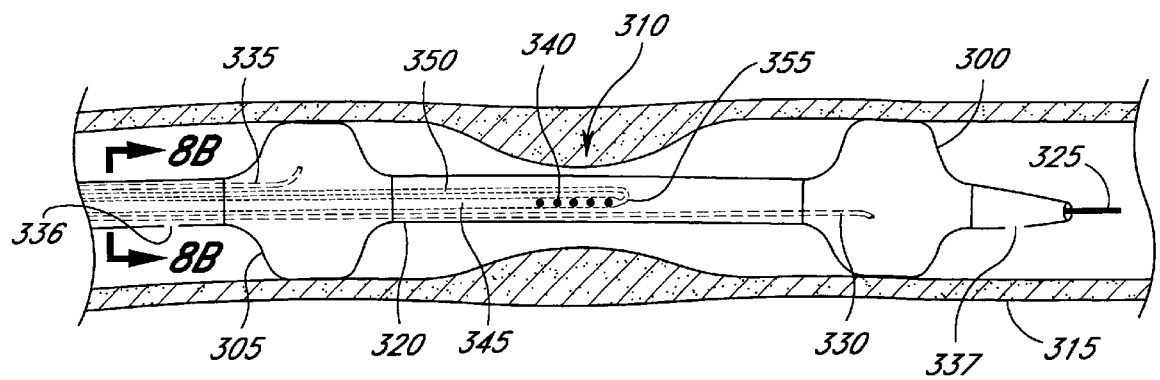
FIG. 8A is a longitudinal cross sectional view of an embodiment utilizing two, independently inflatable balloons.
Figure 8B:
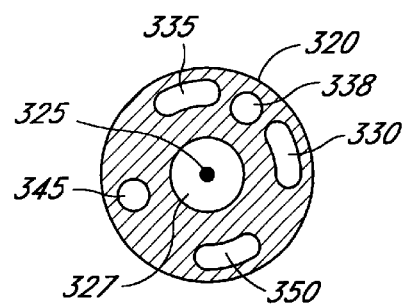
FIG. 8B is an end cross sectional view of the embodiment of FIG. 8A.

Referring now to FIGS. 8A and 8B, an alternative embodiment of the present invention is shown, in which a first balloon 300 and a second balloon 305 bracket a stenosis site 310 within a vessel 315 during treatment, each balloon preferably being located within 4 cm of that site. The balloons 300 and 305 are joined to a radiation catheter 320 through which a guidewire 325 passes, which is preferably similar in construction to guidewire 221. The radiation catheter 320 preferably has an O.D. of 0.070–0.120" and is preferably 120–130 cm in length (e.g., 100 cm of 73D Pebax™ adjoining 20–30 cm of 35D Pebax™). The guidewire 325 is located within a guidewire lumen 327 and is useful in positioning the radiation catheter 320 at the stenosis site 310. As shown in FIG. 8A, balloons 300 and 305 are in fluid communication with respective inflation lumens 330 and 335, respectively, so that they can be independently inflated and deflated after being positioned within the vessel 315, thus permitting more accurate control of the balloons and reducing the risk of damaging healthy tissue. To permit the perfusion of blood, the radiation catheter 320 preferably has two perfusion holes 336 and 337 located at respective ends of the radiation catheter, in which the holes 336 and 337 are connected by a perfusion lumen 338, which is shown in FIG. 8B.

As in the embodiment of FIGS. 2A and 2B and the other embodiments herein, radiation may be delivered to the stenosis site 310 in a number of ways, e.g., by bonding a radioactive source directly onto the radiation catheter 320, or by injecting either a radioactive fluid or more preferably a fluid that contains radioactive carriers 340 into a lumen 345. When injected into the radiation catheter 320, the fluid passes through the injection lumen 345 and then into a vent lumen 350 before leaving the radiation catheter 320. However, the injection lumen 345 preferably has a constriction 355 (FIGS. 9A and 9B) therein so that the radioactive carriers 340 stop at the stenosis site 310. After the stenosis site 310 has been treated, the radioactive carriers 340 can be forced back out of the patient by injecting fluid into the vent lumen 350 and back out the injection lumen 345.

Figure 9A:
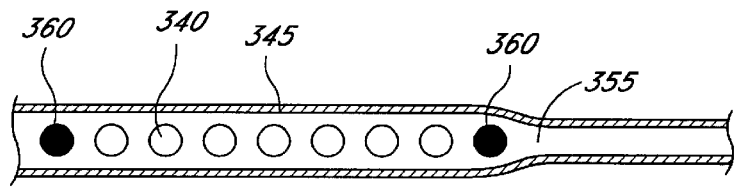
FIGS. 9A and 9B illustrate spherical and cylindrical radiopaque carriers, respectively, within an injection lumen for delivering radiation to a stenosis site.
Figure 9B:
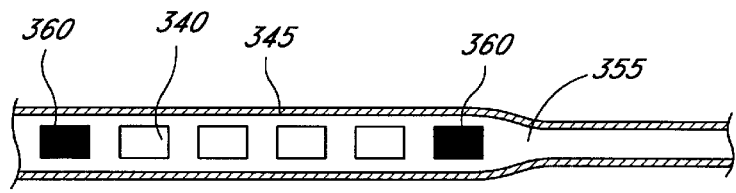
Figure 9C:
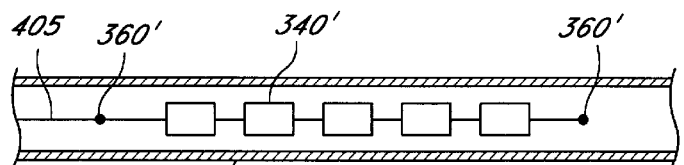
FIG. 9C illustrates an alternative way of delivering radiation to a stenosis site, in which the radiopaque and radioactive carriers are fastened to a wire.

As shown in FIG. 9B, the radioactive carriers 340 may be cylindrical (between 0.010 and 0.040" in diameter and between 0.020 and 0.200" in length), or as illustrated in FIG. 9A, they may be spherical. If the radioactive carriers 340 are of other oblong shapes, they are preferably constructed such they can be easily injected into and retrieved from the injection lumen 345. The injection lumen 345 is preferably circular in cross section and 0.021–0.025" in diameter before the constriction 355, at which point it may taper down to only 0.010–0.015" in diameter. The first and last particles 360 in the train of radioactive carriers 340 are preferably radiopaque, and may comprise gold or platinum, to aid in locating the position of the radioactive carriers 340 during visual fluoroscopy. Alternatively, the radiation may be delivered as shown in FIG. 9C, in which radiopaque carriers 360' and radioactive carriers 340' are fastened to a pull wire 405 for insertion into an injection lumen 345'. This technique obviates the need for a vent lumen.

Figure 10A:
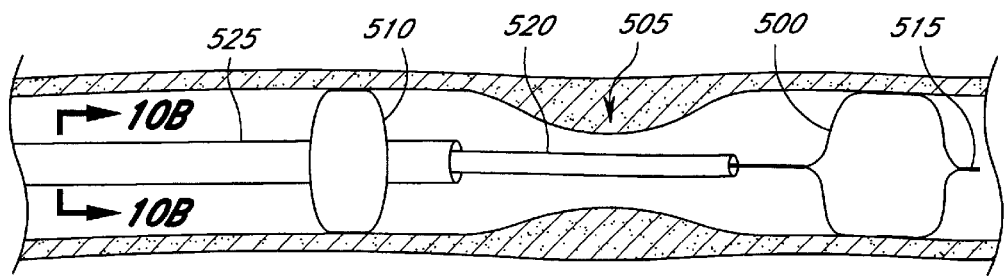
FIG. 10A is a longitudinal cross sectional view of an embodiment utilizing two balloons, in which the distal balloon is tied to a guidewire and the proximal balloon to a proximal catheter.
Figure 10B:
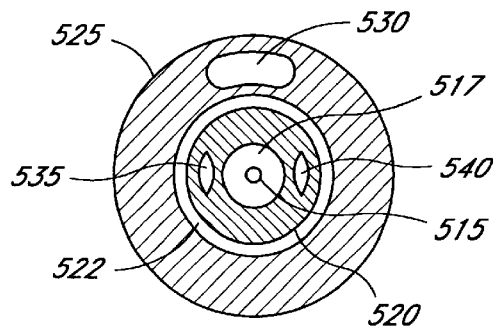
FIG. 10B is an end cross sectional view of the embodiment of FIG. 10A.

Another embodiment utilizing two balloons is illustrated in FIGS. 10A and 10B, in which balloons 500 and 510 are on the distal and proximal sides of the stenosis site 505, respectively. The distal balloon 500 is attached to a guidewire 515 that passes through a guidewire lumen 517 within a catheter 520, the catheter being used for delivering radiation to the stenosis site 505 and having its own lumen 522. The proximal balloon 510, on the other hand, is attached to a proximal catheter 525 that surrounds the radiation catheter 520. Thus, the distance separating the two balloons 500 and 510 is variable, giving the clinician added flexibility when centering the radiation catheter 520 within the vessel at the stenosis site. Further, the balloons 500 and 510 are independently inflatable, the distal balloon 500 preferably being in fluid communication with the interior of the guidewire 515, and the proximal balloon 510 being in fluid communication with an inflation lumen 530 within the proximal catheter 525. Radiation is preferably delivered to the stenosis site 505 using fluid that contains radioactive carriers. An injection lumen 535 and a vent lumen 540 function similar to their counterparts in FIGS. 8A and 8B. Alternatively, a radiation source can be fastened directly to the radiation catheter 520, as in the embodiments of FIGS. 2A and 2B, or to a wire, as in FIG. 9C.

5. Balloon at or Near the Stenosis Site

Figure 11A:
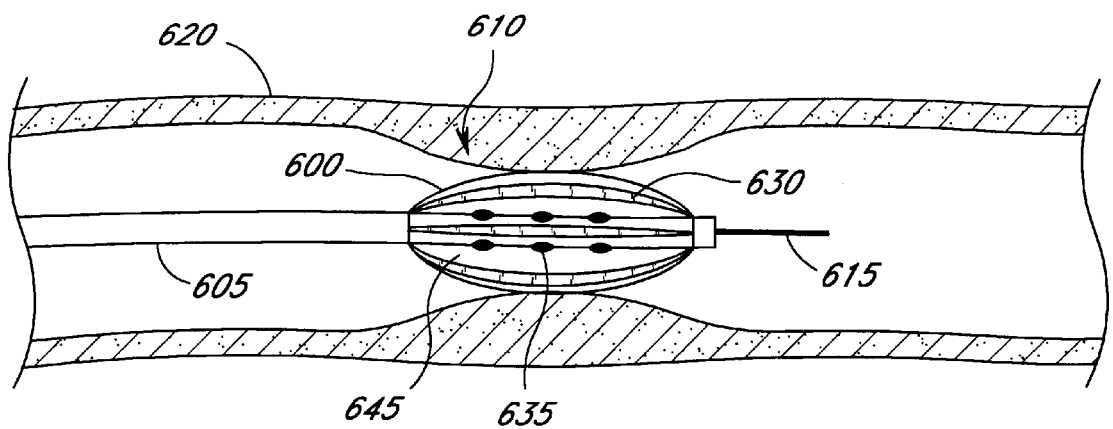
FIG. 11A is a longitudinal cross sectional view of an embodiment utilizing a balloon placed at the stenosis site, in which a radioactive source within the balloon is exposed to the vessel as the balloon expands.
Figure 11B:
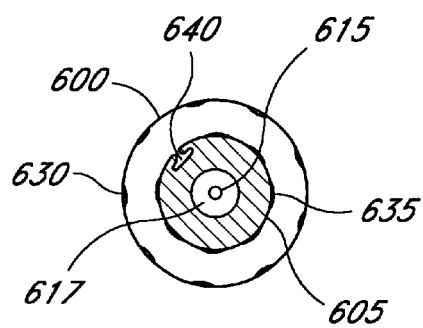
FIG. 11B is an end cross sectional view of the embodiment of FIG. 11A.

FIGS. 11A and 11B show another embodiment of the invention, in which a balloon 600 is attached to a catheter 605 that delivers radiation to a stenosis site 610. A guidewire 615 within a lumen 617 in the catheter 605 facilitates proper placement of the catheter within the vessel 620. The balloon 600 has radiopaque strips 630 thereon which substantially enclose a radiation source 635 to shield the surroundings when the balloon is not inflated. The strips 630 are preferably gold or platinum. The balloon 600 is preferably connected to an inflation lumen 640 running through the radiation catheter 605, so that as the balloon is inflated, the strips 630 move away from the radiation catheter 605, opening up uncovered portions 645 of the balloon between the strips to expose the stenosis site 610 to the radioactive source 635. The radioactive source 635 may be mounted directly to the radiation catheter 605 as indicated in FIG. 11B or be delivered through lumens in the form of radioactive carriers, as discussed in connection with the embodiments of FIGS. 8A, 8B, 9A, 9B, 9C, 10A, and 10B.

Figure 12:
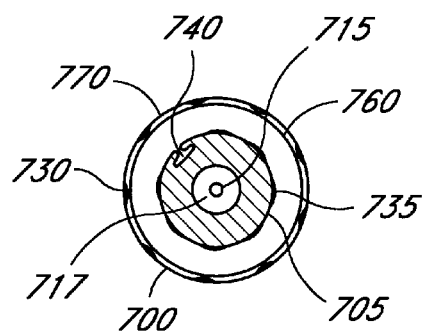
FIG. 12 is end cross sectional view of an embodiment similar to that of FIG. 11A and 11B, in which an inner balloon is inflated to expand an outer balloon.

An embodiment similar to that of FIGS. 11A and 11B is shown in FIG. 12, in which an inner balloon 760 that is preferably noncompliant is inflated to contact and expand a slitted outer balloon 700. The outer balloon 700 has slits 770 between radiopaque strips 730 of preferably gold or platinum, the slits being gaps in the outer balloon that, for example, may have been cut out of the outer balloon.

When the inner balloon 760 is not inflated, the strips 730 of the outer balloon 700 form a substantially radiopaque shield around a radiation source 735. When the inner balloon 760 is inflated, however, the strips 730 of the outer balloon move away from each other and the radiation source 735 so that the strips are separated by the slits 770. As the outer balloon 700 expands, the slits 770 increase in area so that radiation passes through the slits to treat a stenosis site. The inner balloon 760 may be inflated until the outer balloon 700 contacts the vessel to be treated so that the radiation source 735 is centered in the vessel. The embodiment of FIG. 12 also includes a radiation catheter 705, a guidewire 715, a guidewire lumen 717, and an inflation lumen 740 which function substantially like their counterparts in FIGS. 11A and 11B. In the embodiments of FIGS. 11A, 11B, and 12, the balloons 600 and 700 may be periodically deflated and rotated, so that the stenosis site is more uniformly irradiated (i.e., so that portions of the stenosis site occluded by the radiopaque strips 630 and 730 are irradiated).

Radiation Centering Embodiments Using One or More Expandable Structures

The embodiments discussed below are similar to the previously discussed embodiments, except that expandable structures are employed rather than inflatable balloons. The expandable structures can comprise, for example, coils, ribs, a ribbon-like structure, a slotted tube, a filter-like mesh, or a braid. The expandable structures are preferably "spring-like" in nature, i.e. they are preferably resilient to facilitate their deployment or retraction. In addition, the expandable structures may optionally be radially asymmetrical with respect to the radiation catheter to which they are joined, such that treatment is delivered asymmetrically within the vascular segment. Any one of a number of ways may be used to secure the expandable structures to their respective sheaths, catheters, etc., such as welding, adhesives, or using rings to hold them in place. As in the previous embodiments, the radioactive source used in the expandable structure embodiments below may be secured directly onto the radiation catheter or delivered to the stenosis site through a lumen, e.g., a radioactive fluid, a fluid containing radioactive carriers, or a wire to which radioactive carriers are fastened. Details regarding intravascular occlusive devices are described in Assignee's co-pending U.S. application Ser. No. 09/026,106, filed Feb. 19, 1998, entitled OCCLUSION OF A VESSEL, which is hereby incorporated by reference.

1. A Single Distal Braid

Figure 13A:
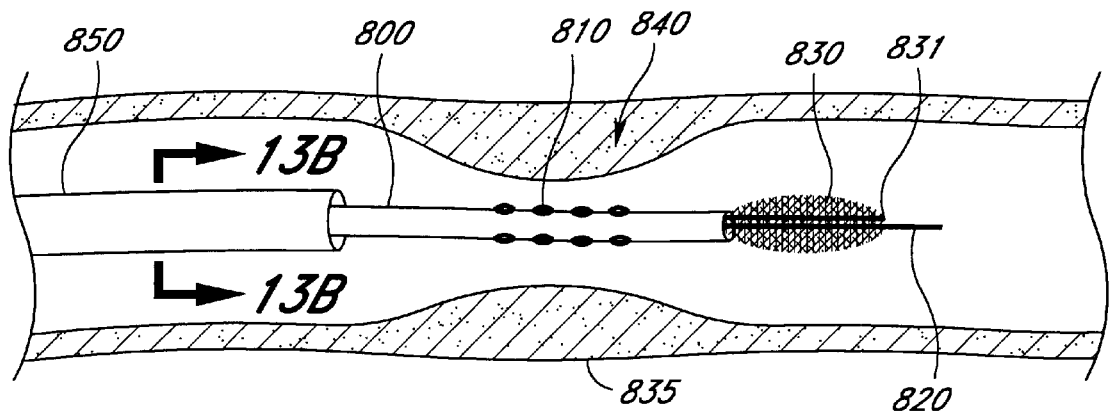
FIG. 13A is a longitudinal cross sectional view of an embodiment in which an expandable structure (a braid) is used to center a radiation catheter within a vessel to be treated.
Figure 13B:
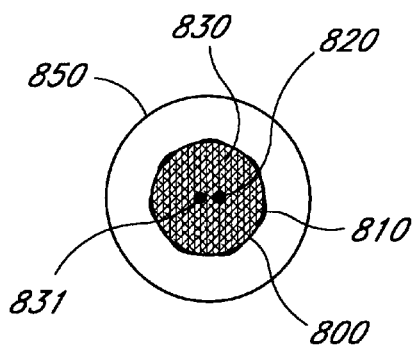
FIG. 13B is an end cross sectional view of the embodiment of FIG. 13A.

In FIGS. 13A and 13B, for example, an embodiment is disclosed that is substantially analogous to that shown in FIGS. 2A and 2B. A radiation catheter 800 delivers a radioactive source 810 to a stenosis site 840, and a guidewire 820 within the radiation catheter aids the clinician in properly positioning the radiation catheter within the vessel 835 to be treated. A shield catheter 850 may be used to protect the surroundings and personnel from unwanted radioactive exposure.

Figure 14A:
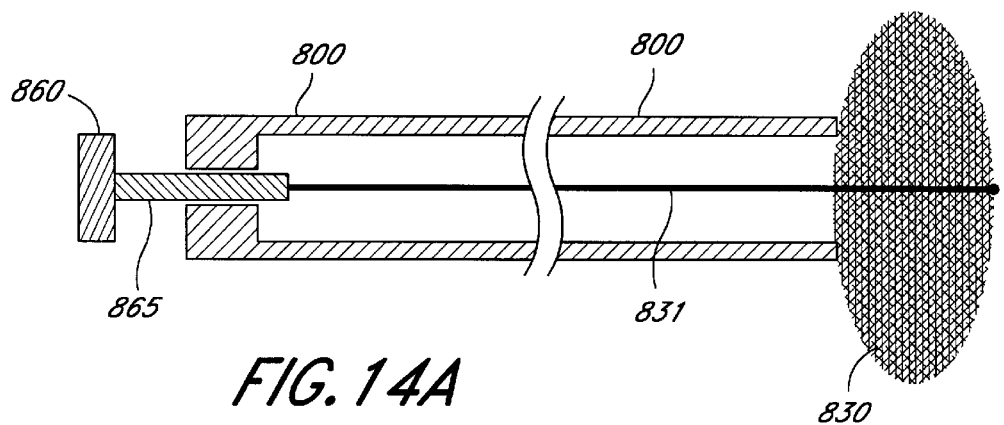
FIGS. 14A and 14B show longitudinal and end perspective views, respectively, of a locking mechanism used with a wire that deploys an expandable structure (in this case, a braid).

An expandable structure (in this embodiment, a braid) 830 is preferably attached on its proximal end to the guidewire 820 and can be deployed, for example, with a pull wire 831 that passes through the radiation catheter 800. The braid 830 is shown in FIGS. 13A and 13B in the undeployed position and in FIG. 14A in the deployed position. When the braid 830 is deployed, it acts to center the radiation catheter 800 within the vessel 835 near the stenosis site 840. The braids of these embodiments are preferably Elgiloy™, Nitinol, or stainless steel, preferably resilient, and are preferably either thin wires of 0.002–0.010" diameter, or tiny ribbons of 0.002–0.005" in thickness and 0.005–0.010" in width. The braid 830 of FIGS. 13A, 13B, and 14A is shown as being the type that is deployed with a pull wire 831, but a self-expanding braid, such as that shown in FIGS. 15, 16A, and 16B can also be used. The braid 830 is preferably porous enough to facilitate the perfusion of blood.

Figure 14B:
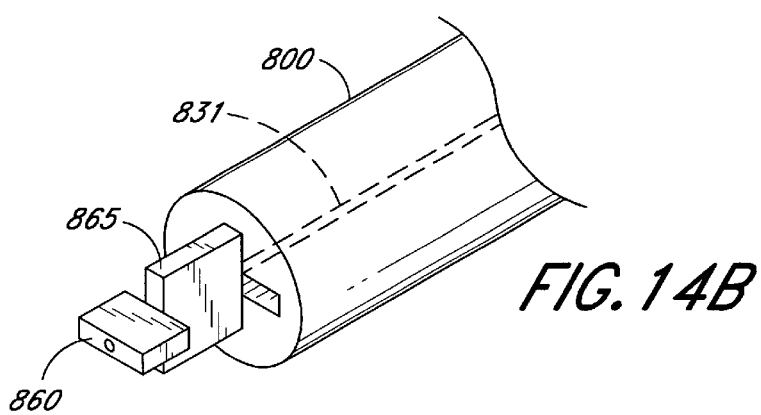

A preferred way of deploying the pull wire type braid 830 is shown in FIGS. 14A and 14B. FIG. 14A illustrates the braid 830 being deployed by the pull wire 831, which is attached to the distal end of the braid. A rotatable handle 860 is attached to a locking element 865 which in turn is fastened to the pull wire 831. When the locking element 865 clears the catheter 800 within which it resides (which is preferably outside the patient), the locking element and rotatable handle 860 may be oriented as illustrated in FIG. 14B to keep the pull wire 831 taught, thereby preventing the braid 830 from returning to its undeployed position. The pull wire may be made of stainless or nitinol and may have a diameter of 0.006–0.008 inches.

Figure 14C:
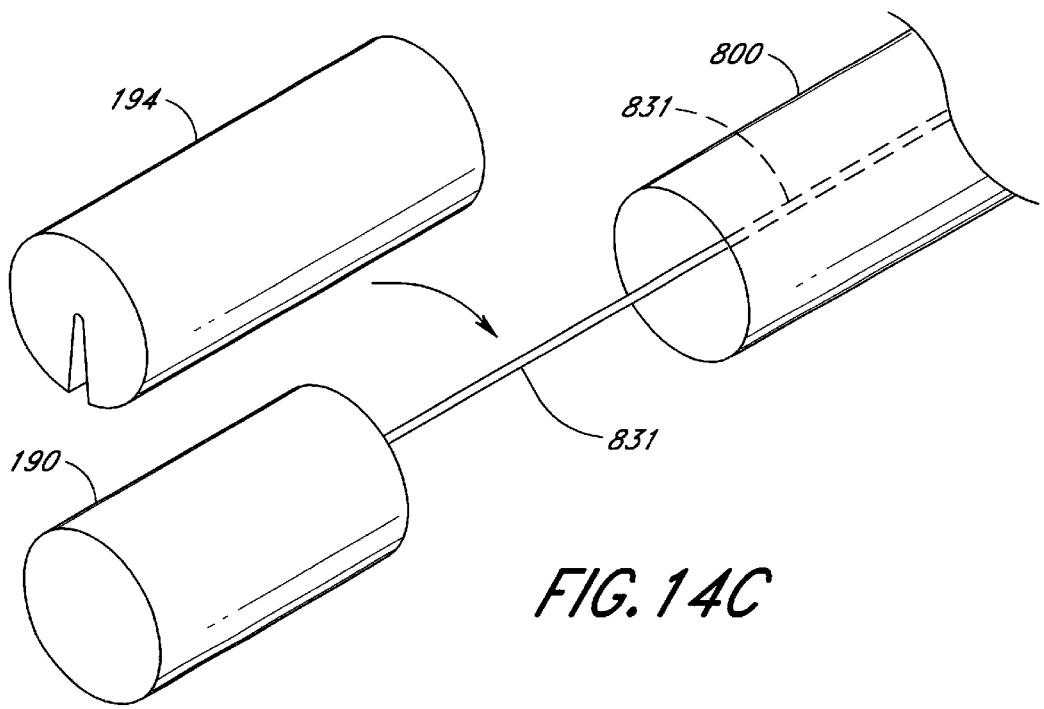
FIG. 14C is a perspective view of an alternative locking mechanism used with a wire that deploys an expandable structure.

An alternative to the deployment apparatus illustrated in FIGS. 14A and 14B is shown in FIG. 14C, in which a handle member 190 is grasped by the clinician to retract the pull wire 831, thereby deploying the expandable structure. Once extended, the expandable structure preferably has the tendency to return to its undeployed position, which in the process pulls the pull wire 831 back into the catheter 800. This can be prevented by inserting a spacer member 194 between the handle member 190 and the catheter 800. After the medical procedure is complete, and occlusion of the vessel is no longer required, the spacer member 194 can be removed and the pull wire 831 and the expandable mechanism returned to their respective undeployed positions. The device can then be removed from the patient.

2. A Plurality of Braids

Figure 15:
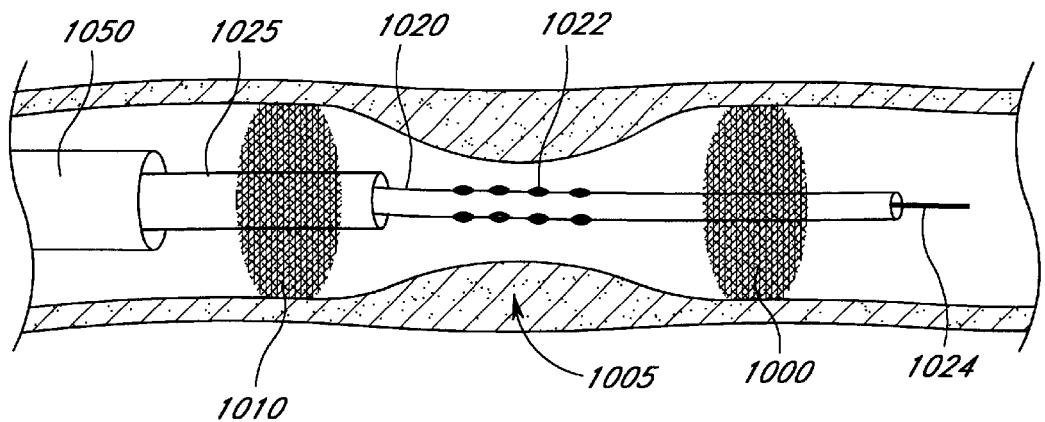
FIG. 15 is an embodiment utilizing two expandable structures (in this case, braids), in which the expandable structures adjoin separate catheters.

Another embodiment illustrating the use of braids is illustrated in FIG. 15, which is substantially analogous to the two-balloon embodiment of FIGS. 10A and 10B. A distal braid 1000 and a proximal braid 1010 are preferably positioned on either side of a stenosis site 1005. When deployed as in FIG. 15, the braids 1000 and 1010 secure a radiation catheter 1020 and its radiation source 1022, so that the stenosis site 1005 can be uniformly irradiated. A guidewire 1024 aids the clinician in positioning the radiation catheter 1020 within the patient. The distal braid 1000 in this embodiment is attached to the radiation catheter 1020, whereas the proximal braid 1010 may be secured to a proximal catheter 1025. Although pull wire braids can be used in this embodiment and in the embodiment of FIGS. 16A and 16B below, braids 1000 and 1010 are illustrated as being self-expanding. For example, the braids 1000 and 1010 may fit within a sheath 1050 before they are deployed, and be collapsed by the sheath 1050 after treatment but before the device is removed from the patient. Alternatively, proximal sheath 1025 may act as a sheath for the distal braid 1000, alternately deploying and collapsing it.

Figure 16A:
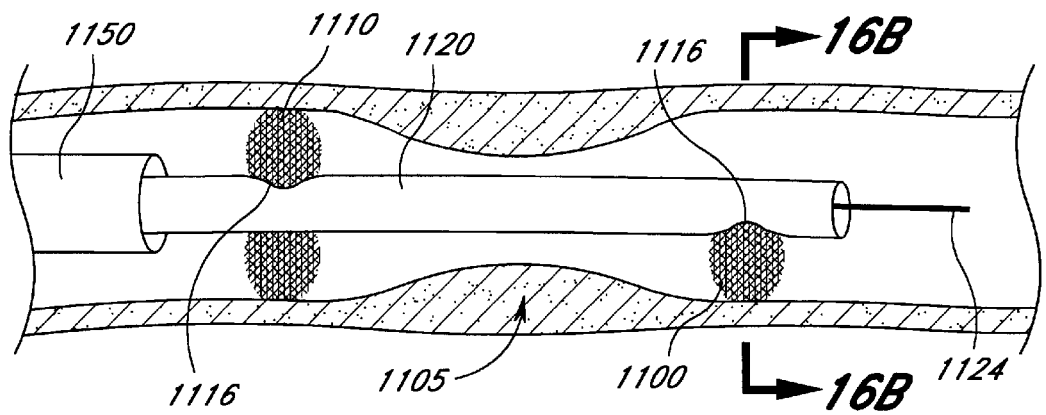
FIG. 16A is an embodiment utilizing two expandable structures (in this case, braids), in which the expandable structures adjoin the same catheter.
Figure 16B:
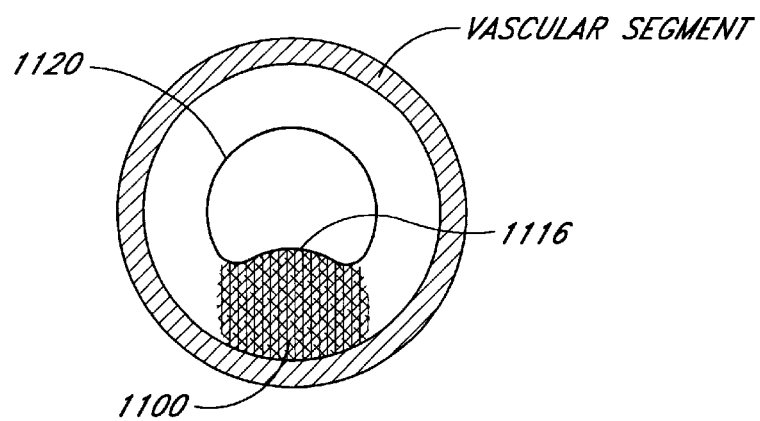
FIG. 16B is an end cross sectional view of the embodiment of FIG. 16A.

An alternative two-braid embodiment is shown in FIGS. 16A and 16B, in which two self-expanding braids are used, a distal braid 1100 and a proximal braid 1110 that surround a stenosis site 1105 to be treated. The braids 1100 and 1110 are shown in the deployed position and are attached to indentations 1116 on a radiation catheter 1120 (preferably made of Nylon, polyethylene, or Pebax™:), so that the braids do not extend in the radial direction substantially beyond where the radiation catheter 1120 would extend if it were not dented. A sheath 1150 is used for alternately deploying and collapsing the braids 1100 and 1110. When they are deployed, the braids 1100 and 1110 help center the radiation catheter 1120 within the vessel to be treated. A guidewire 1124 aids the clinician in positioning the radiation catheter 1120 within the patient. As discussed in connection with the previous embodiments, radiation can be delivered, for example, through lumens within the radiation catheter 1120 (e.g. radioactive fluid, radioactive carriers within a fluid, or radioactive carriers fastened to a wire) or by using a radioactive source attached directly to the radiation catheter.

The self-expanding braids 1100 and 1110 are shown in FIGS. 16A and 16B as extending less than 360 degrees around the radiation catheter 1120, thereby reducing the risk of clot formation and permitting blood to flow around the braids. For example, the distal braid 1100 is illustrated in FIG. 16B as supporting the radiation catheter 1120, but its radial extent around the radiation catheter is limited. Likewise, the proximal braid 1110 extends only partially around the radiation catheter 1120.

3. Other Expandable Structures

The embodiments below also center a radiation delivering device in a vessel. It will be understood by those in the art that the following embodiments can be combined with the various radiation delivery technologies disclosed herein to form intravascular radiation therapy devices, especially self-centering devices. In particular, the flexible elongate members discussed below may be catheters such as radiation catheters.

Figure 17:
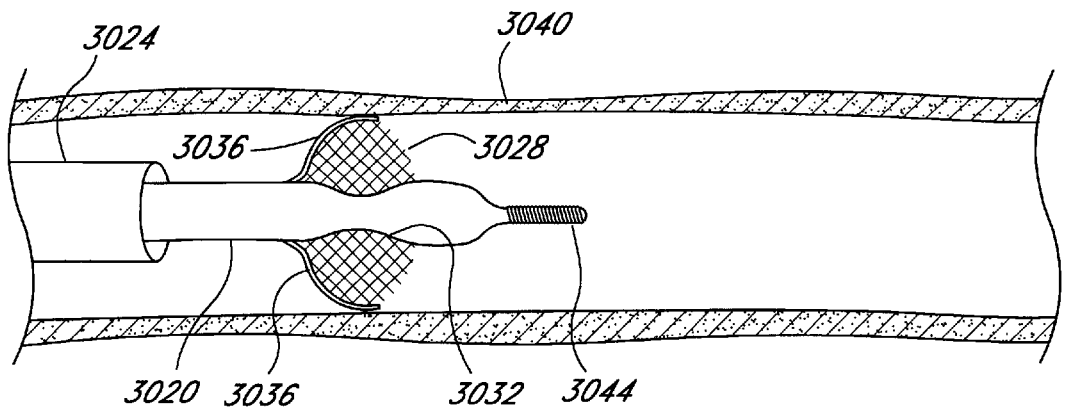
FIG. 17 is a schematic, longitudinal cross sectional view of an embodiment in which a membrane only partially surrounds a braid used as the expandable structure.

Another embodiment using a braided structure is shown schematically in FIG. 17, in which a flexible elongate member 3020 is disposed within a second elongate member 3024 such as a hypotube. A self expanding mechanism 3028 such as a braided structure is secured to the distal end of the elongate member 3020, preferably within an indentation 3032 of member 3020, and centers one or both of the flexible elongate members 3020 and 3024 within the patient's vessel 3040. The braided structure 3028 may be partially encapsulated by a preferably elastomeric membrane 3036 that contacts the patient's vessel 3040 and protects the vessel from abrasion. (Alternatively, a coating such as a polymeric coating may used in place of the membranes disclosed herein.) In this and the other embodiments, adhesive may be used to secure the self-expanding mechanism 3028 and the membrane 3036 to the elongate member 3020. In the embodiment of FIG. 17, the braided structure 3028 and membrane 3036 are designed to be asymmetrical, with more material being concentrated at the proximal side of the structure 3028. The braids of the embodiments disclosed herein may be stainless steel 304 or 400, superelastic or heat activated Nitinol, or a polymer base, such as polyethylene or polypropylene. They may be constructed, for example, by using standard equipment such as a braider.

Although the embodiment of FIG. 17 shows the flexible elongate member 3020 connected to a guidewire tip 3044, other technologies for guiding the device through the patient's vessel 3040 may be used in this and the following embodiments, such as a guidewire (either over the wire or single operator) or the exchange catheter method, as is well known in the art. Also, although not explicitly shown in the embodiment of FIG. 17 and the other embodiments herein, these embodiments may include various lumens (e.g., for delivering radiation), aspiration and irrigation fittings, and collars.

Figure 18A:
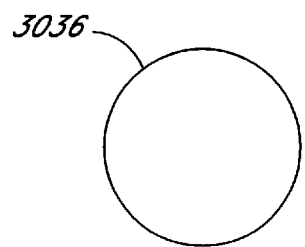
FIGS. 18A and 18B show end views of unperforated and perforated membranes, respectively.
Figure 18B:
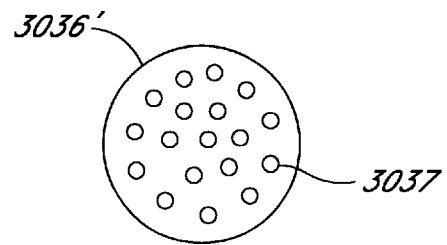

Although the membrane 3036 may be impervious to the flow of blood (FIG. 18A) for those applications not requiring perfusion, a perforated membrane 3036' (FIG. 18B) having numerous holes 3037 therein is preferably used in other applications to allow the passage of blood. The holes 3037 are preferably greater than 10 microns in diameter and may be up to 80 microns or more in diameter to permit the passage of blood cells (nominally 6–10 microns in diameter) through the membrane 3036' while blocking larger particulates such as emboli. Likewise, a perforated membrane 3036' is preferably used in the following embodiments. Antithrombogenic coatings can be used (e.g., heparin) to prevent thrombosis formation.

Figure 19:
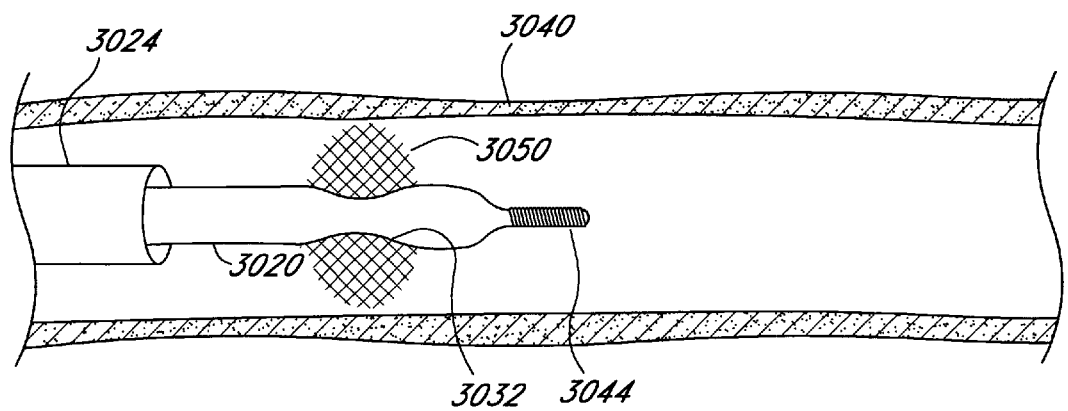
FIG. 19 is a schematic, longitudinal cross sectional view of an embodiment in which a braid without a membrane is used.

FIG. 19 shows a self-centering embodiment in which a braided structure 3050 is not enclosed by a membrane. When the braided structure 3050 comprises, for example, a diamond mesh pattern in which adjacent wires are separated by about 10–80 microns, the braided structure permits the passage of red blood cells, while blocking the flow of matter that may be undesirable, e.g., emboli or other particulates that may be formed or dislodged during medical procedures. Thus, this embodiment is well suited for applications for perfusion.

Figure 20:
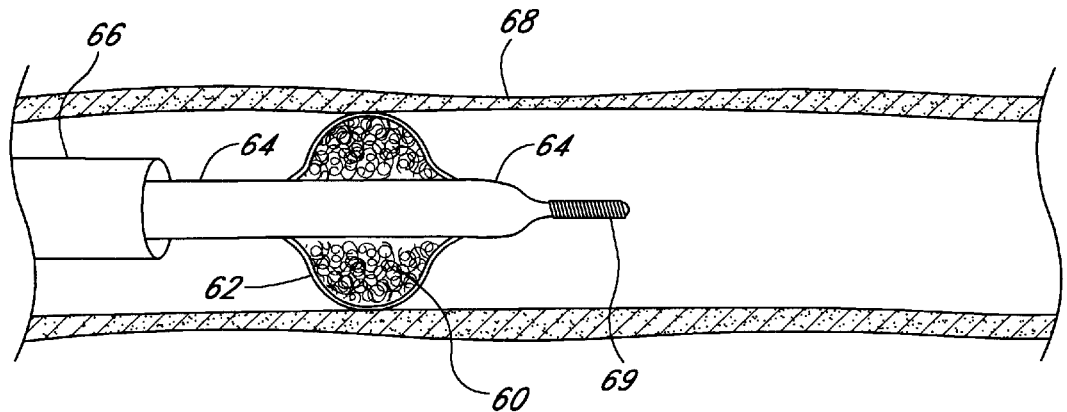
FIG. 20 is a schematic, longitudinal cross sectional view of an embodiment in which a filter-like mesh is used as the expandable structure.
Figure 21:
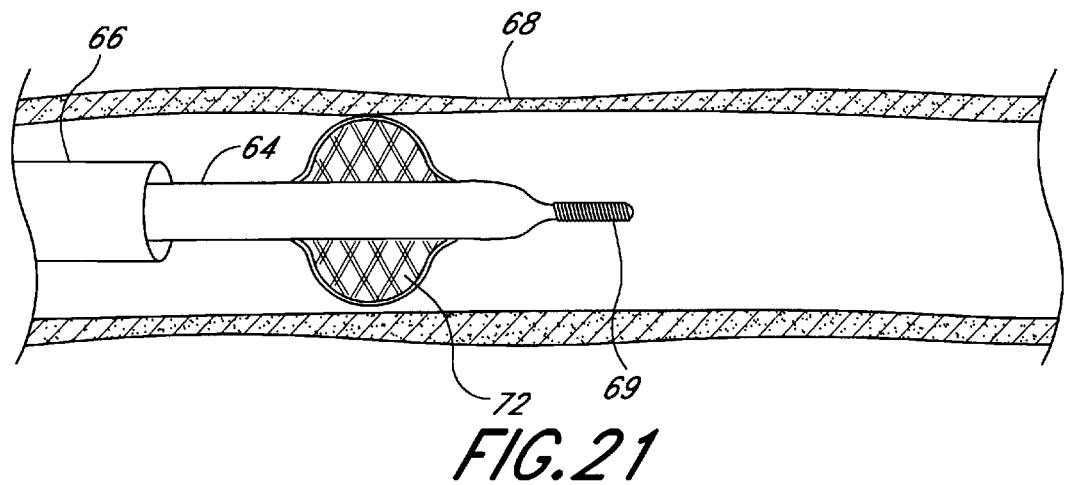
FIG. 21 is a schematic, longitudinal cross sectional view of an embodiment in which a slotted tube is used as the expandable structure.
Figure 22:
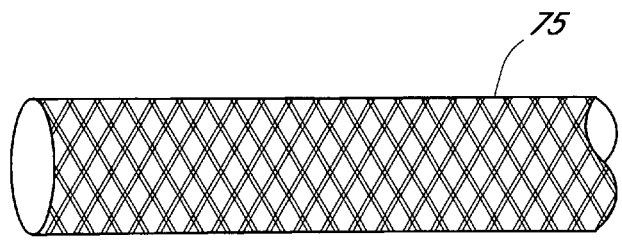
FIG. 22 is a perspective view of the slotted tube used in the embodiment of FIG. 21.

Alternative self-expanding media for self-centering are shown in FIGS. 20 and 21. In FIGS. 20 and 21, a self-expanding filter-like mesh 60 and a self-expanding slotted tube 72, respectively, may be optionally surrounded by a membrane 62 that is preferably perforated and elastomeric. The filter-like mesh 60 (or slotted tube 72) and membrane 62 are bonded or otherwise secured to a flexible elongate member 64, e.g., to an indentation therein. As with the other self-expanding media disclosed herein, the filter-like mesh 60 (or slotted tube 72) expands from its unexpanded state when the flexible elongate member 64 is pushed through a second elongate member 66, or alternatively, when the second elongate member 66 is retracted over the first elongate member 64. The filter-like mesh 60 (or slotted tube 72) then expands so that the membrane 62 (if one is used) contacts the surrounding vessel 68 to center one or both of the flexible elongate members 64 and 66, one of which is preferably a radiation catheter. A guidewire tip 69 aids in guiding the device through the vessel 68. The filter-like mesh 60 and slotted tube 72 are of a suitable shape memory material such as Nitinol or (304 or 400) stainless steel. The filter-like mesh 60 is analogous to steel wool, whereas the slotted tube 72 is like a stent in appearance. The slotted tube 72 may be constructed, for example, by irradiating a thin-walled tube with a laser beam to form holes in the tube in the shape of polygons such as oblong quadrilaterals. An unexpanded, slotted tube 75 is shown in FIG. 22.

Figure 23:
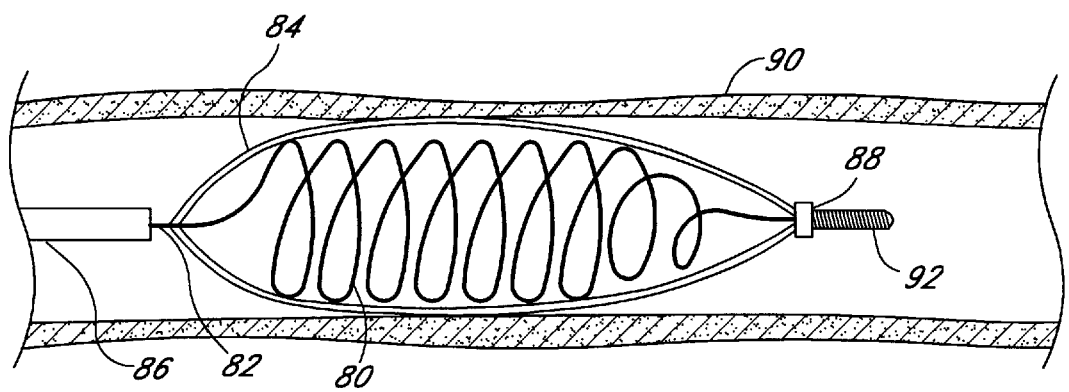
FIG. 23 is a schematic, longitudinal cross sectional view of an embodiment in which a coil is used as the expandable structure, and the proximal end of a membrane surrounding the coil adjoins the coil.

FIG. 23 illustrates another self-centering embodiment, in which a coil 80 serves as the self-expanding mechanism. The coil 80 (which may be radioactive or have radioactive material fastened to it) may be integrally formed with a first elongate member 82 (such as a radioactive wire) or be otherwise specially joined to it, e.g., by welding or brazing the coil to the elongate member 82. The coil 80 may be surrounded by a preferably perforated membrane 84 that expands with the coil when it is pushed out of a second elongate member 86 (which may be a radiation catheter), or alternatively, when the second elongate member 86 is retracted from the coil 80. Thus, the membrane 84 (if one is used) contacts the surrounding vessel 90. The membrane 84 may be attached directly to the first elongate member 82, or to a member 88 such as a disk that is in turn secured to the coil 80 or the first elongate member 82. A guidewire tip 92 for guiding the device through the vessel 90 may be attached to the first elongate member 82 or to the member 88, if one is used.

Figure 24:
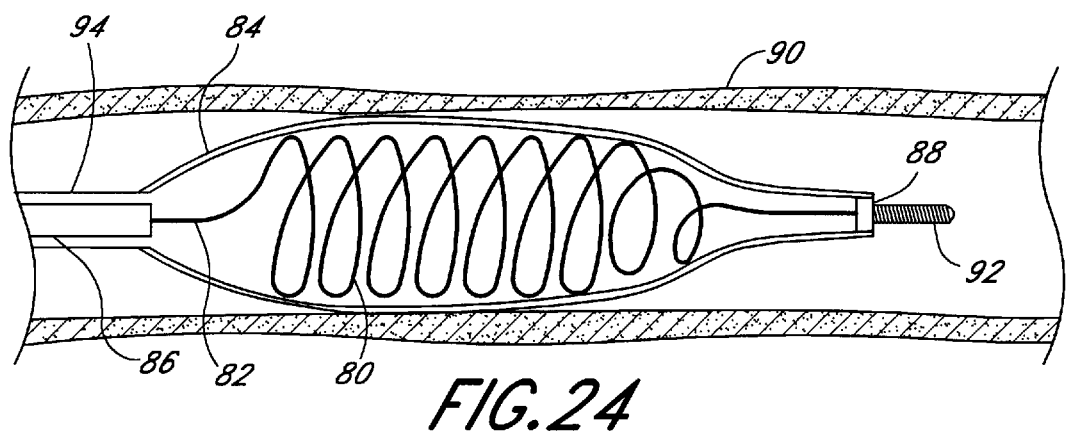
FIG. 24 is a schematic, longitudinal cross sectional view of an embodiment in which a coil is used as the expandable structure, and the proximal end of a membrane surrounding the coil adjoins a sheath that surrounds both first and second elongate members.

An embodiment similar to that shown in FIG. 23 is illustrated in FIG. 24, in which the membrane 84 is secured at the proximal end to a separate sheath 94. In this case, the sheath 94 and the first elongate member 82 are retracted together over the second elongate member 86, or alternatively, they may be respectively pushed over and through the second elongate member.

Figure 25:
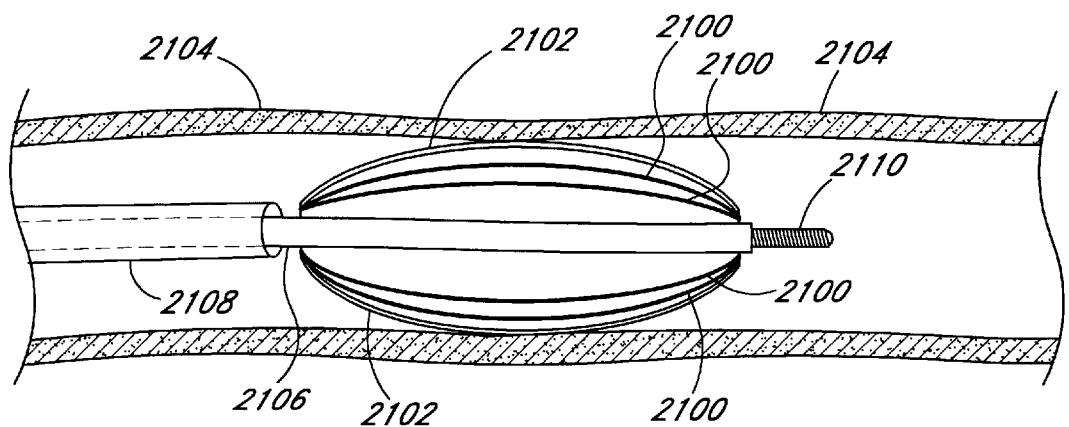
FIG. 25 is a schematic, side cross sectional view of an embodiment in which a plurality of ribbons are used as the expandable structure.

Another embodiment for centering a radiation therapeutic device within a vessel that employs a self-expanding medium is shown in FIG. 25, in which a plurality of ribbons 2100 contact a vessel wall 2104 or a (preferably perforated) membrane 2102 to urge the membrane towards the wall of the vessel 2104. The ribbons 2100 of this embodiment are preferably secured to a first elongate member 2106 at both ends of the ribbons, by, for example, gluing them in place. The ribbons may be 0.001–0.004"×0.005–0.020"×0.25–1.0" strips of Nitinol, stainless steel, or Elgiloy™, which expand when urged out of the second elongate member 2108. A guidewire tip 2110 may be used for guiding the device through the vessel and is preferably secured to the distal end of the first elongate member 2106. The first elongate member 2106 or the second elongate member 2108 may be a radiation catheter.

Figure 26:
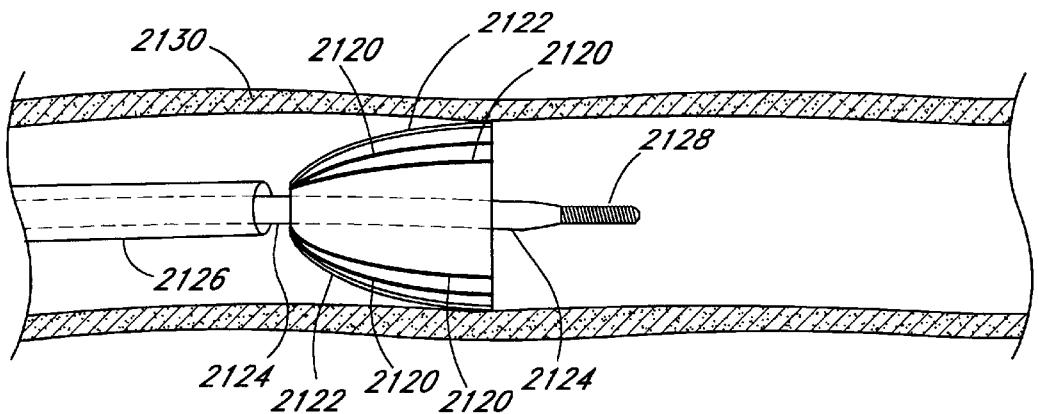
FIG. 26 is a schematic, side cross sectional view of an embodiment in which a plurality of ribs are used as the expandable structure.

FIG. 26 illustrates an embodiment similar to the one in FIG. 25, in which ribs 2120 such as wires form a series of semicircular arcs when expanded. The ribs 2120 may be surrounded by a (preferably perforated) membrane 2122 that expands with the ribs to contact the vessel 2130 to center the device within the vessel 2130. The number of ribs 2120 is preferably at least three. The ribs 2120 are preferably attached directly, to a first elongate member 2124 that is surrounded by a second elongate member 2126, either of which may be a radiation catheter. The ribs 2120 themselves are preferably made of a shape memory material such as Nitinol or stainless steel. A guidewire tip 2128 aids in guiding the device through the vessel 2130.

As in the other self-expanding embodiments, the self-expanding mechanism 2100 (2120) is in an unexpanded state when enclosed by the second elongate member 2108 (2126), and expands when pushed or pulled beyond the second elongate member 2108 (2126).

Figure 27:
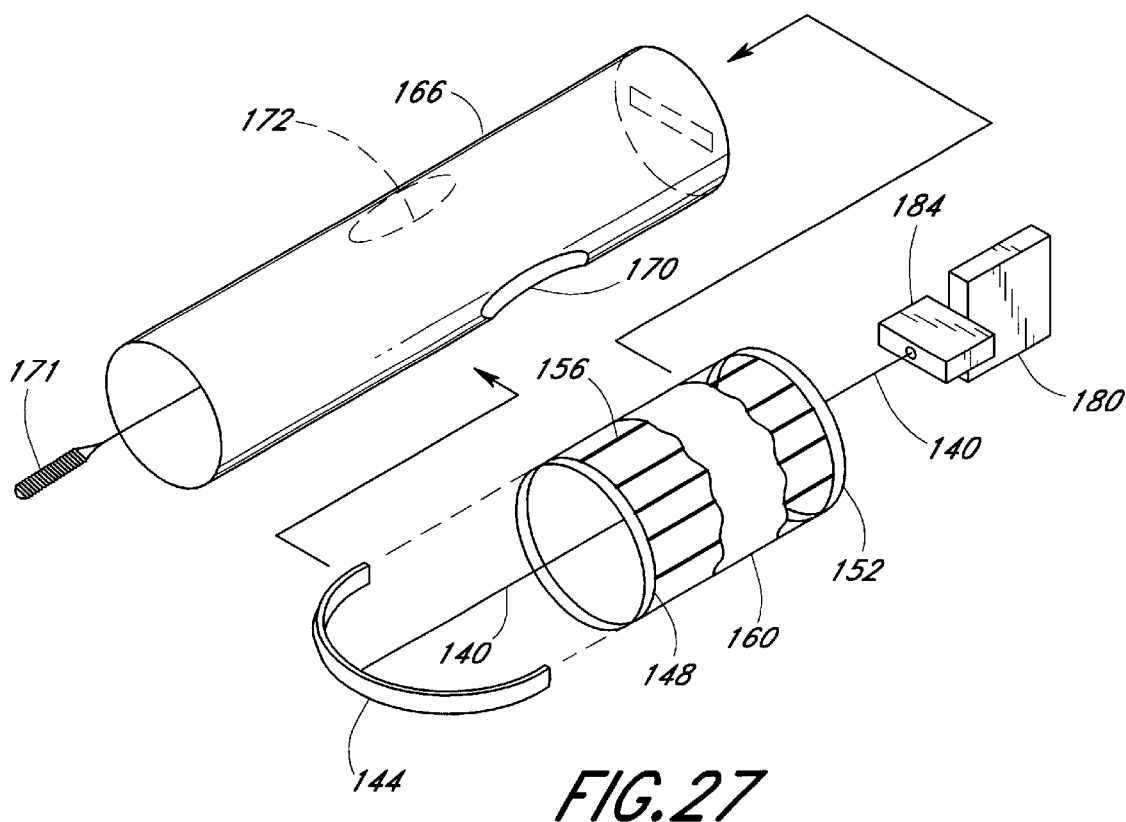
FIG. 27 is an isometric view of an embodiment of the invention in which a pull wire is used to deploy a plurality of nonself-expanding ribbons surrounded by a membrane.
Figure 28:
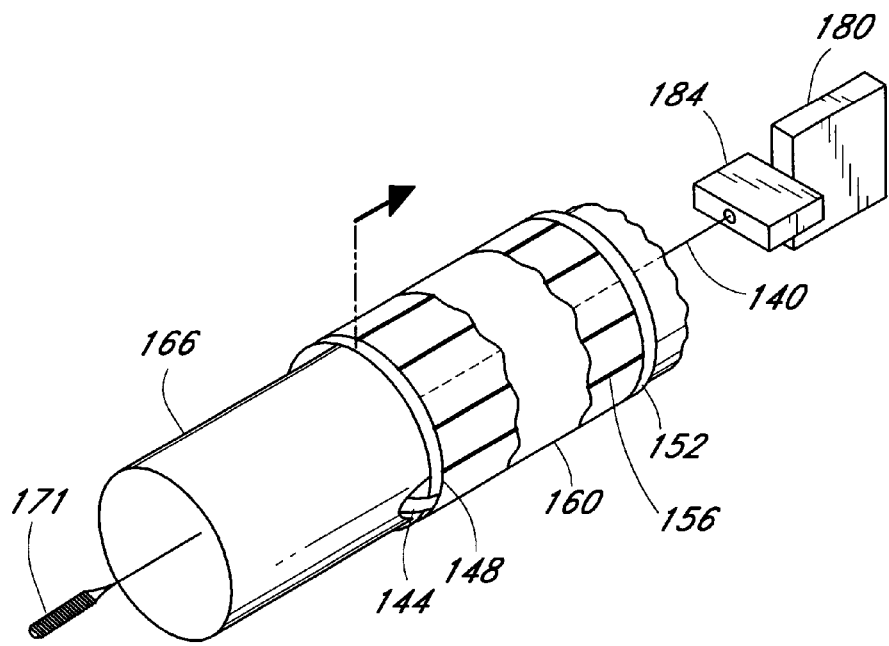
FIG. 28 is a side partial sectional view of the embodiment of FIG. 27 in which the ribbons are in their relaxed, undeployed position.
Figure 29:
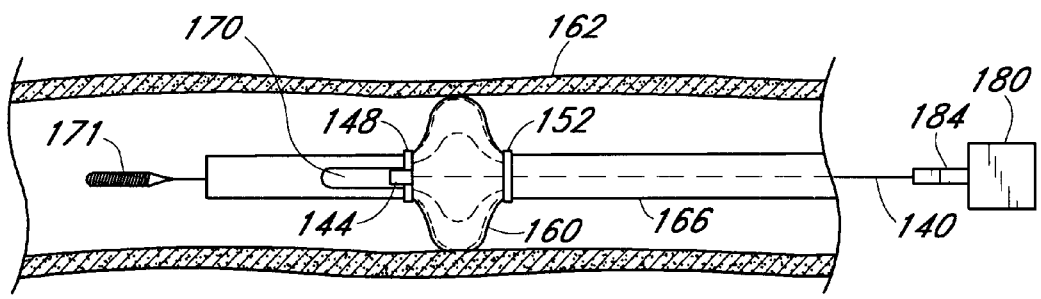
FIG. 29 is a side elevational view of the embodiment of FIG. 27 in which the ribbons are deployed, and the membrane contacts the vessel.

Centering mechanisms that are not self-expanding can also be used to center a radiation delivery device (such as a catheter) within a vessel, as is described below. In the embodiment of FIGS. 27–29, a first elongate member 140, preferably a pull wire, is (when the device is completely assembled) attached to a brace member 144 that is in turn attached to a first ring member 148. Adjoining the first ring member 148 and a second ring member 152 are a plurality of ribbons 156 that extend between the two ring members. Surrounding the ribbons 156 there may be a (preferably perforated) membrane 160 (shown in partial cutaway in FIGS. 27, 28, 30A, 30B, 30C, and 30D) that contacts the patient's vessel 162 when the ribbons are expanded. If it is used, the membrane 160 is joined to at least one and preferably both of the ring members 148 and 152. The membrane 160 can be joined to only one of the ring members 148 and 152, for example, when the membrane 160 extends far enough in the longitudinal direction to permit the membrane to contact the vessel 162 when the ribbons 156 are deployed.

To assemble the device, the first and second ring members 148 and 152, the ribbons 156, and the membrane 160 are placed as a unit around a second elongate member 166, which has a pair of oppositely facing holes 170 and 172. The second elongate member 166 may be a radiation catheter, for example. The brace member 144 is inserted through the holes 170 and 172 and secured to both the pull wire 140 and the first ring member 148. Further, the second ring member 152 is secured to the second elongate member 166. This assembled configuration, with the ribbons 156 in their longitudinal orientation, is illustrated in FIG. 28. As illustrated in FIG. 29, when the pull wire 140 is retracted, the ribbons 156 (shown in phantom) and the membrane 160 that surrounds them are urged towards the vessel 162, where the membrane contacts the vessel to center the second elongate member 166. The ribbons 160 are preferably resilient enough that they return to their longitudinal orientation when the pull wire 140 is released. The elasticity and resilience of the pull wire 140 also helps the ribbons 156 return to their undeployed configuration., A guidewire tip 171 may be used to assist in guiding the device to the desired location in the vessel 162. Preferred ways of deploying guidewires are discussed above in connection with FIGS. 14A, 14B, and 14C.

Although the principle of using a nonself-expanding mechanism has been illustrated in FIGS. 27–29 with respect to deformable ribbons, other nonself-expanding mechanisms can be employed in conjunction with the brace member 144 and the first and second ring members 148 and 152. For example, instead of using ribbons 156, a nonself-expanding braided structure 200 can be used, in which the braided structure 200 adjoins first and second ring members 148 and 152 and is optionally covered with a preferably perforated membrane 160 (to allow perfusion) to form the unit 204 shown in FIG. 30A. The unit 204 can be used in conjunction with an elongate member 166, a brace member 144, a guidewire tip 171, a first elongate member 140 such as a pull wire, a rotatable handle 180, and a locking member 184 to form a device analogous to the ribbon-based device of FIG. 27. Alternatively, other mechanisms can be used for securing the pull wire 140, such as a handle member 190 and a spacer member 194.

Figure 30A:
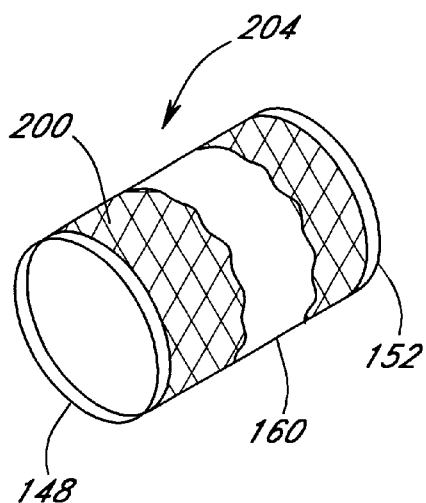
FIGS. 30A, 30B, 30C, and 30D show, respectively, a braid, a filter-like mesh, a slotted tube, and a plurality of coils, which can be used as alternative expandable structures in place of the ribbons in the embodiment of FIG. 27. The respective membranes are shown in partial cross section.
Figure 30B:
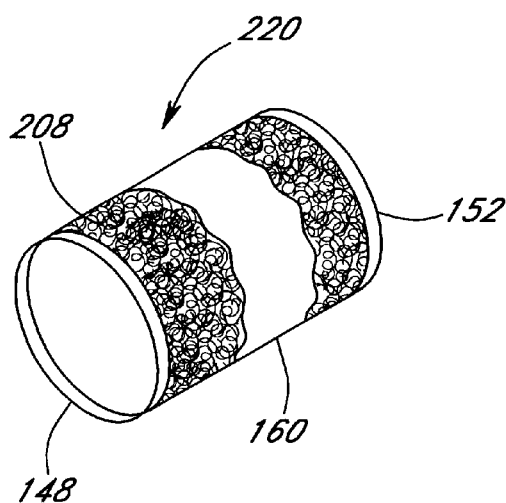
Figure 30C:
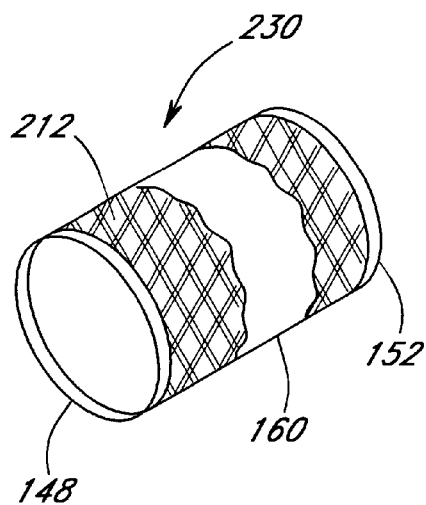
Figure 30D:
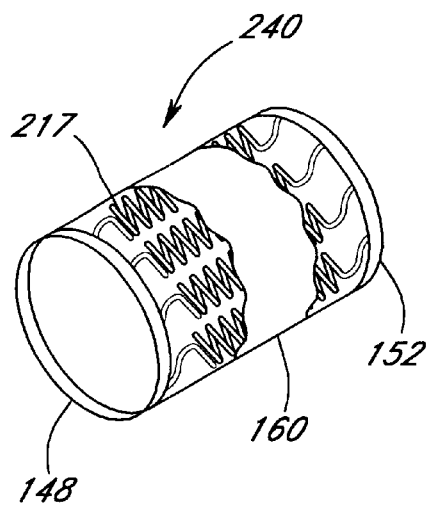

Other nonself-expanding mechanisms such as a filter-like or fibrous mesh 208, a slotted tube 212, and coils 217 can be used to form units 220, 230, and 240 analogous to the braided structure unit 204, as shown in FIGS. 30B–30D. Units 220, 230, and 240 can likewise be used to construct devices analogous to the ribbon-based device illustrated in FIGS. 27–29. Further, if unit 204 is used without a membrane, it may assist in blood perfusion if the braided structure 200 is suitably constructed. Alternatively, perforated membranes like membranes 3036' of FIG. 18B may assist in blood perfusion. Although the ribbons 156, the braided structure 200, the filter-like mesh 208, the slotted tube 212, and the coils 217 must be actively deployed (e.g. with a pull wire 140), they are nevertheless similar to their self-expanding counterparts.

Figure 31:
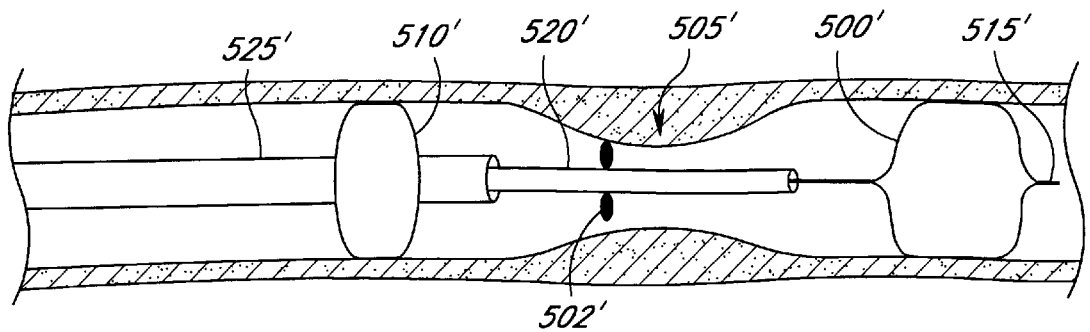
FIG. 31 is a longitudinal cross sectional view of an atherectomy device.

The centering technology disclosed herein can be utilized in other procedures, such as in atherectomy, as shown in FIG. 31, which shows an embodiment that is analogous in many respects to the embodiment of FIG. 10A. A proximal catheter 525' surrounds an atherectomy catheter 520' to which a boring mechanism 502' is attached. When the atherectomy catheter 520' rotates, the boring mechanism 502' engages a stenosis site 505' to widen the constriction. The device may be centered with distal and proximal balloons 500' and 510', or alternatively, with expandable structures such as those disclosed herein. A guidewire 515' may be used when positioning the device within the vessel.

Figure 32:
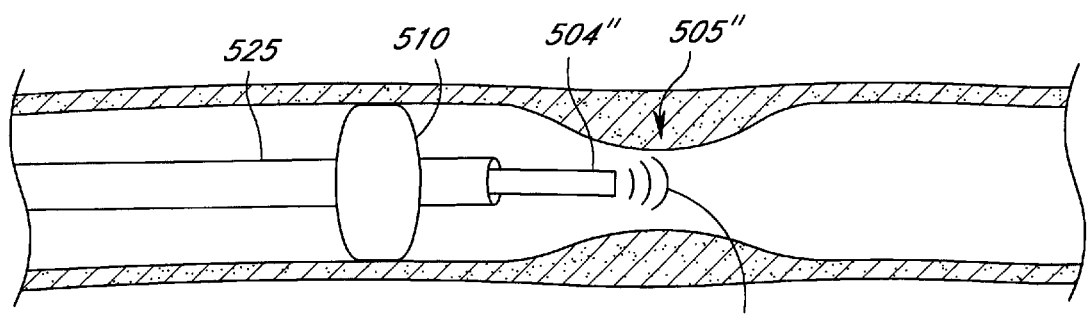
FIG. 32 is a longitudinal cross sectional view of a device that uses a laser.

Another application of the centering technology disclosed herein is illustrated in FIG. 32, in which a laser beam 503" is preferably directed through a fiber optic 504" onto a vessel or a vessel's stenosis site 505". A proximal balloon 510" (alternatively, an expandable structure such as that disclosed herein) may be used to position, aim, or center the device. The balloon 510" is preferably secured to a proximal catheter 525".

It should be understood that the scope of the present invention is not to be limited by the illustrations or the foregoing description thereof, but rather by the appended claims, and certain variations and modifications of this invention will suggest themselves to one of ordinary skill in the art.

What is claimed is:

1. A device for treating a segment of a vessel in a patient, comprising:

a catheter for delivering radiation;

an elongate inner guidewire sized to fit within said radiation catheter, said radiation catheter sliding on said inner guidewire such that said inner guidewire guides said radiation catheter to said segment of the vessel;

at least one expandable structure at a distal end portion of said inner guidewire, said inner guidewire and said expandable structure configured such that said expandable structure can be positioned distal to said segment; and a radioactive source for treating the vascular segment, said radioactive source at a distal end portion of said radiation catheter, wherein said expandable structure supports both said distal end portion of said inner guidewire and said distal end portion of said radiation catheter to generally center said distal end portion of said radiation catheter within the vessel.

2. The device of claim 1, in which said at least one expandable structure is one expandable structure.

3. The device of claim 1, wherein said guidewire is hollow.

4. A method of treating a segment in a vessel, comprising:

inserting an elongate inner member into the vessel;

expanding at least one expandable structure at a distal end portion of the inner member to support the distal end portion of the inner member in the vessel, such that the expanded structure is in contact with the vessel but distal to the segment to be treated;

providing a catheter having radiation material;

guiding the catheter over the inner member so that the radiation material is within said segment of the vessel; and treating the vascular segment by exposing it to radiation.

5. The method of claim 4, further comprising:

contracting the expandable structure after treatment; and removing the expandable structure and the catheter from the vessel.

6. A radiation device for treating a segment of a vessel in a patient, comprising:
   a catheter;
   a guidewire within said catheter for directing said catheter through the vessel, said guidewire comprising a centering device for generally centering said guidewire within the vessel; and
   a radioactive source fastened directly onto said catheter.

7. The device of claim 6, further comprising a retractable shield that surrounds said radioactive source when the vascular segment is not being treated.

8. The device of claim 6, in which said radioactive source is bonded onto said catheter.

9. The device of claim 1, wherein said guidewire comprises Nitinol.

10. The device of claim 1, wherein said expandable structure comprises a balloon.

11. The device of claim 10, wherein said balloon is inflated with fluid that passes through said inner guidewire.

12. The device of claim 10, wherein said balloon is compliant.

13. The device of claim 1, further comprising a sheath for shielding the vessel from radiation when said segment is not being treated.

14. The method of claim 4, said treating the vascular segment comprising retracting a sheath to expose said segment to radiation.

15. The method of claim 4, comprising positioning the expandable structure distal to and within about 4 cm of said segment during treatment.

16. The method of claim 4, wherein the expandable structure comprises a balloon.

17. The method of claim 16, said expanding comprising inflating the balloon with fluid.

18. The method of claim 4, wherein the inner member comprises a guidewire.

19. The method of claim 18, wherein the guidewire is hollow.

20. The method of claim 18, wherein the guidewire comprises Nitinol.

21. A device for treating a segment of a vessel in a patient, comprising:
   a non-inflatable catheter for delivering radiation;
   an elongate inner member sized to fit within said radiation catheter, said radiation catheter sliding on said inner member such that said inner member guides said radiation catheter to said segment of the vessel;
   at least one expandable structure at a distal end portion of said inner member for securing said inner member within the vessel; and
   a radioactive source for treating the vascular segment, said radioactive source at a distal end portion of said radiation catheter,
   wherein said expandable structure supports said distal end portion of said inner member to generally center said distal end portion of said radiation catheter within the vessel.

22. A device for treating a segment of a vessel in a patient, comprising:
   a catheter for delivering radiation;
   an elongate inner member sized to fit within said radiation catheter, said radiation catheter sliding on said inner member such that said inner member guides said radiation catheter to said segment of the vessel;
   at least one expandable structure at a distal end portion of said inner member for securing said inner member within the vessel; and
   a radioactive source for treating the vascular segment, said radioactive source at a distal end portion of said radiation catheter,
   wherein said expandable structure supports said distal end portion of said inner member to generally center said distal end portion of said radiation catheter within the vessel and to position said radioactive source at the center of the vessel.

23. A device for treating a segment of a vessel in a patient, comprising:
   a catheter for delivering radiation;
   an elongate member that slides relative to said radiation catheter;
   an expandable structure at a distal end portion of said member for securing said member within the vessel; and
   a radioactive source for treating the vascular segment, said radioactive source at a distal end portion of said radiation catheter,
   wherein said expandable structure supports said distal end portion of said member to generally center said distal end portion of said radiation catheter within the vessel when one of said expandable structure and said source is distal to and spaced apart from the other of said expandable structure and said source.

24. A method of treating a segment in a vessel, comprising:
   inserting an elongate inner member into the vessel;
   expanding at least one expandable structure at a distal end portion of the inner member to support the distal end portion of the inner member in the vessel;
   providing a non-inflatable catheter having radiation material;
   guiding the catheter over the inner member so that the radiation material is within said segment of the vessel; and
   treating the vascular segment by exposing it to radiation.

25. A method of treating a segment in a vessel, comprising:
   inserting an elongate inner member into the vessel;
   expanding at least one expandable structure at a distal end portion of the inner member to support the distal end portion of the inner member in the vessel;
   providing a catheter having radiation material;
   guiding the catheter over the inner member so that the radiation material is within said segment of the vessel and positioned at the center of the vessel; and
   treating the vascular segment by exposing it to radiation.

26. The device of claim 21, wherein said elongate member is hollow.

27. The device of claim 21, wherein said elongate member comprises Nitinol.

28. The device of claim 21, wherein said expandable structure comprises a balloon.

29. The device of claim 28, wherein said balloon is inflated with fluid that passes through said elongate member.

30. The device of claim 28, wherein said balloon is compliant.

31. The device of claim 21, further comprising a sheath for shielding the vessel from radiation when said segment is not being treated.

32. The device of claim 22, wherein said elongate member is hollow.

33. The device of claim 22, wherein said elongate member comprises Nitinol.

34. The device of claim 22, wherein said expandable structure comprises a balloon.

35. The device of claim 34, wherein said balloon is inflated with fluid that passes through said elongate member.

36. The device of claim 34, wherein said balloon is compliant.

37. The device of claim 22, further comprising a sheath for shielding the vessel from radiation when said segment is not being treated.

38. The device of claim 23, wherein said elongate member is hollow.

39. The device of claim 23, wherein said elongate member comprises Nitinol.

40. The device of claim 23, wherein said expandable structure comprises a balloon.

41. The device of claim 40, wherein said balloon is inflated with fluid that passes through said elongate member.

42. The device of claim 40, wherein said balloon is compliant.

43. The device of claim 23, further comprising a sheath for shielding the vessel from radiation when said segment is not being treated.

44. The method of claim 24, further comprising:
   contracting the expandable structure after treatment; and
   removing the expandable structure and the catheter from the vessel.

45. The method of claim 24, said treating the vascular segment comprising retracting a sheath to expose said segment to radiation.

46. The method of claim 24, comprising positioning the expandable structure distal to and within about 4 cm of said segment during treatment.

47. The method of claim 24, wherein the expandable structure comprises a balloon.

48. The method of claim 24, wherein the inner member comprises a guidewire.

49. The method of claim 48, wherein the guidewire is hollow.

50. The method of claim 48, wherein the guidewire comprises Nitinol.

51. The method of claim 25, further comprising:
   contracting the expandable structure after treatment; and
   removing the expandable structure and the catheter from the vessel.

52. The method of claim 25, said treating the vascular segment comprising retracting a sheath to expose said segment to radiation.

53. The method of claim 25, comprising positioning the expandable structure distal to and within about 4 cm of said segment during treatment.

54. The method of claim 25, wherein the expandable structure comprises a balloon.

55. The method of claim 25, wherein the inner member comprises a guidewire.

56. The method of claim 55, wherein the guidewire is hollow.

57. The method of claim 55, wherein the guidewire comprises Nitinol.

* * * * *